United States Patent
Liang et al.

(10) Patent No.: US 11,596,377 B2
(45) Date of Patent: Mar. 7, 2023

(54) SYSTEM AND METHOD FOR RADIATION EXPOSURE CONTROL

(71) Applicant: SHANGHAI UNITED IMAGING HEALTHCARE CO., LTD., Shanghai (CN)

(72) Inventors: Kan Liang, Shanghai (CN); Wei Li, Shanghai (CN); Dingche Tang, Shanghai (CN); Yan Wang, Shanghai (CN)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 136 days.

(21) Appl. No.: 17/134,588

(22) Filed: Dec. 28, 2020

(65) Prior Publication Data

US 2021/0121152 A1    Apr. 29, 2021

Related U.S. Application Data

(63) Continuation of application No. PCT/CN2019/093406, filed on Jun. 27, 2019.

(30) Foreign Application Priority Data

Jun. 27, 2018   (CN) .......................... 201810676483.5

(51) Int. Cl.
  *A61B 6/00*   (2006.01)
  *A61B 6/02*   (2006.01)
  *A61B 6/03*   (2006.01)

(52) U.S. Cl.
  CPC .............. *A61B 6/542* (2013.01); *A61B 6/025* (2013.01); *A61B 6/032* (2013.01); *A61B 6/502* (2013.01); *A61B 6/548* (2013.01); *A61B 6/563* (2013.01)

(58) Field of Classification Search
  CPC ......... A61B 6/025; A61B 6/032; A61B 6/502; A61B 6/542; A61B 6/548; A61B 6/563
  See application file for complete search history.

(56) References Cited

U.S. PATENT DOCUMENTS

| 2004/0061081 A1* | 4/2004 | Murakoshi ........... G01N 23/046 250/591 |
| 2005/0041772 A1 | 2/2005 | Nishide |

(Continued)

FOREIGN PATENT DOCUMENTS

| CN | 103713215 A | 4/2014 |
| CN | 103919569 A | 7/2014 |

(Continued)

OTHER PUBLICATIONS

International Search Report in PCT/CN2019/093406 dated Oct. 9, 2019, 5 pages.

(Continued)

*Primary Examiner* — Blake C Riddick
(74) *Attorney, Agent, or Firm* — Metis IP LLC

(57) ABSTRACT

The present disclosure directs to a system and method for controlling a radiation exposure on a subject. The method includes obtaining exposure instructions including an exposure state of an imaging device. The method also includes determining first components associated with the imaging device and one or more target operations of the first components corresponding to the exposure state. The method further includes generating target operation instructions based on the one or more target operations of the first components. The method still further includes controlling the first components to implement the target operation instructions.

16 Claims, 13 Drawing Sheets

(56) References Cited

U.S. PATENT DOCUMENTS

| | | | |
|---|---|---|---|
| 2006/0202127 A1* | 9/2006 | Ozeki | A61B 6/548 250/370.01 |
| 2006/0291624 A1* | 12/2006 | Xue | H04N 5/32 348/E5.081 |
| 2007/0297569 A1* | 12/2007 | Saunders | A61B 6/00 378/108 |
| 2008/0240366 A1 | 10/2008 | Bacher et al. | |
| 2010/0054624 A1* | 3/2010 | Nishino | A61B 6/4283 378/91 |
| 2010/0078583 A1* | 4/2010 | Tsubota | A61B 6/548 250/580 |
| 2010/0135464 A1* | 6/2010 | Nishino | G01T 1/00 378/114 |
| 2010/0207032 A1* | 8/2010 | Tsubota | G01T 1/17 250/370.09 |
| 2010/0208958 A1* | 8/2010 | Yamada | A61B 6/4435 382/128 |
| 2011/0135057 A1 | 6/2011 | Mori et al. | |
| 2011/0170662 A1* | 7/2011 | Baumgart | A61B 6/504 378/62 |
| 2012/0018640 A1* | 1/2012 | Shimizukawa | G01T 1/16 250/354.1 |
| 2012/0018641 A1* | 1/2012 | Watanabe | A61B 6/4233 250/354.1 |
| 2012/0163534 A1* | 6/2012 | Nambu | A61B 6/487 378/44 |
| 2013/0028381 A1* | 1/2013 | Sung | G01T 1/247 378/62 |
| 2013/0062527 A1* | 3/2013 | Hyde | A61N 5/1071 250/366 |
| 2013/0166245 A1* | 6/2013 | Samari | H04L 67/10 709/217 |
| 2013/0170615 A1 | 7/2013 | Wei et al. | |
| 2013/0336444 A1* | 12/2013 | Kuwabara | A61B 6/10 378/62 |
| 2014/0056408 A1* | 2/2014 | Tajima | G01T 1/2018 378/116 |
| 2014/0112446 A1 | 4/2014 | Tsuchiya | |
| 2014/0348299 A1* | 11/2014 | Sung | G01T 1/2914 378/91 |
| 2014/0348404 A1* | 11/2014 | Jerebko | G06T 7/0012 382/131 |
| 2015/0078521 A1* | 3/2015 | Ozawa | A61B 6/566 378/62 |
| 2018/0008215 A1 | 1/2018 | Wayama et al. | |

FOREIGN PATENT DOCUMENTS

| | | | |
|---|---|---|---|
| CN | 107773259 A | 3/2018 | |
| CN | 108919608 A * | 11/2018 | A61B 6/00 |
| CN | 109009186 A | 12/2018 | |
| WO | 2020001571 A1 | 1/2020 | |

OTHER PUBLICATIONS

Written Opinion in PCT/CN2019/093406 dated Oct. 9, 2019, 5 pages.

The Extended European Search Report in European Application No. 19824568.0 dated Oct. 28, 2021, 10 pages.

* cited by examiner

SYSTEM AND METHOD FOR RADIATION EXPOSURE CONTROL

CROSS-REFERENCE TO RELATED APPLICATIONS

This application is a continuation of International Patent Application No. PCT/CN2019/093406, filed on Jun. 27, 2019, which claims priority to Chinese Application No. 201810676483.5 filed on Jun. 27, 2018, the contents of which are incorporated entirely herein by reference.

TECHNICAL FIELD

This disclosure generally relates to systems and methods for medical devices, and more particularly, to systems and methods for controlling a radiation exposure of a medical device.

BACKGROUND

With the development of computer science, medical imaging technology has rapidly evolved, and various novel medical imaging devices are being designed and manufactured. Those new medical imaging devices bring about the enormity of changes in operation manners and operation functions, resulting in a high work efficiency. In the meanwhile, there are demands for new methods for controlling the devices.

At present, most imaging systems encapsulate software in traditional manners, which is component-based. In encapsulating control signals based on different components, each control signal for a single component is encapsulated into a signal control method, such that a master control module (also referred to as master control device) of an imaging system may use the signal control method to control each single of the components in a radiation exposure process. The master control device of the imaging system performs normal control sequences, according to timing control requirement of different components, as well as different control methods corresponding to different components, so as to control the components to implement their corresponding functions.

Taking X-ray equipment for mammography as an example, the X-ray equipment for mammography includes a full-field digital mammography (FFDM) device and a digital breast tomosynthesis (DBT). As for digital mammography, its core functions are tomographic imaging, 3D image reconstruction, and application functions of FFDM. The control of flat-panel components is a core factor in a radiation exposure control. FFDM and DBT have different radiation exposure manners, and thus, different types of flat-panel components are used. To control radiation exposure processes of flat-panel components of different types, a designer of an imaging system needs to adopt different control processes and control methods, according to the control characteristics of flat-panel components of different types, resulting in numerous sub-exposure control process of the system, and bringing about difficulties in the system design and maintenance. In addition, due to differences in control sequences of the flat-panel components of different types, it is necessary to consider the compatibility and rationality of those sub-exposure control processes, when synergizing different components, which inconveniences system debugging and maintenance. Thus, it is desirable to provide systems and methods for controlling a radiation exposure process more simply and efficiently.

SUMMARY

According to a first aspect of the present disclosure, a system comprising at least one storage device storing a set of instructions, and at least one processor configured to communicate with the at least one storage device may be provided. When executing the set of instructions, the at least one processor is directed to perform operations including obtaining exposure instructions including an exposure state of an imaging device; determining first components associated with the imaging device and one or more target operations of the first components corresponding to the exposure state; generating target operation instructions based on the one or more target operations of the first components; and controlling the first components to implement the target operation instructions is provided.

In some embodiments, the at least one processor is further directed to perform operations including transmitting state information of the first components to a master control device after the first components preform the one or more target operations.

In some embodiments, the at least one processor is further directed to perform operations including determining a correspondence relationship between exposure states and operations of the first components, and determining the one or more target operations of the first components corresponding to the exposure state based on the correspondence relationship.

In some embodiments, the exposure states are obtained by dividing an exposure process of the radiation exposure on the subject into one or more phases, each of the one or more phases corresponding to an exposure state.

In some embodiments, the exposure states include at least one of an exposure preparation state, an exposure start state, an exposure end state, or an idle state.

In some embodiments, the at least one processor is further directed to perform operations including obtaining information of second components; determining an exposure process of the second components and operations of the second components in the exposure process based on the information of the second components; identifying one or more target operations of the second components corresponding to the exposure state by separating the operations of the second components in the exposure process according to the exposure states; and generating target operation instructions for controlling the second components to implement the one or more target operations.

In some embodiments, the imaging device includes a digital breast tomosynthesis (DBT), a full-field digital mammography (FFDM), a computed tomography (CT) device, a digital radiography (DR), or a computed radiography (CR).

According to a second aspect of the present disclosure, a system comprising at least one storage device storing a set of instructions, and at least one processor configured to communicate with the at least one storage device may be provided. When executing the set of instructions, the at least one processor is directed to perform operations including obtaining exposure triggering parameters; determining an exposure state of an imaging device based on the exposure triggering parameters; generating exposure instructions including the determined exposure state; and transmitting the exposure instructions to first components for controlling the first components to perform one or more target operations corresponding to the exposure state.

According to a third aspect of the present disclosure, a system comprising at least one storage device storing a set of instructions, and at least one processor configured to communicate with the at least one storage device may be provided. When executing the set of instructions, the at least one processor is directed to perform operations including obtaining, by a master control device, exposure triggering parameters; determining, by the master control device, an exposure state of an imaging device based on the exposure triggering parameters; generating, by the master control device, exposure instructions including the determined exposure state; transmitting, by the master control device, the exposure instructions to a component managing device for controlling first components to perform one or more target operations corresponding to the exposure state; obtaining, by the component managing device, the exposure instructions of the exposure state; determining, by the component managing device, one or more target operations of the first components corresponding to the exposure state; generating, by the component managing device, target operation instructions based on the one or more target operations of the first components; and controlling, by the component managing device, the first components to implement the target operation instructions.

According to a fourth aspect of the present disclosure, a method implemented on a computing device having at least one computer readable storage medium storing a set of instructions and at least one processor executing the set of instructions for controlling a radiation exposure on a subject may be provided. The method may include obtaining exposure instructions including an exposure state of an imaging device; determining first components associated with the imaging device and one or more target operations of the first components corresponding to the exposure state; generating target operation instructions based on the one or more target operations of the first components; and controlling the first components to implement the target operation instructions is provided.

According to a fifth aspect of the present disclosure, a method implemented on a computing device having at least one computer readable storage medium storing a set of instructions and at least one processor executing the set of instructions for controlling a radiation exposure on a subject may be provided. The method may include obtaining exposure triggering parameters; determining an exposure state of an imaging device based on the exposure triggering parameters; generating exposure instructions including the determined exposure state; and transmitting the exposure instructions to first components for controlling the first components to perform one or more target operations corresponding to the exposure state.

According to a sixth aspect of the present disclosure, a method implemented on a computing device having at least one computer readable storage medium storing a set of instructions and at least one processor executing the set of instructions for controlling a radiation exposure on a subject may be provided. The method may include obtaining, by a master control device, exposure triggering parameters; determining, by the master control device, an exposure state of an imaging device based on the exposure triggering parameters; generating, by the master control device, exposure instructions including the determined exposure state; transmitting, by the master control device, the exposure instructions to a component managing device for controlling first components to perform one or more target operations corresponding to the exposure state; obtaining, by the component managing device, the exposure instructions of the exposure state; determining, by the component managing device, one or more target operations of the first components corresponding to the exposure state; generating, by the component managing device, target operation instructions based on the one or more target operations of the first components; and controlling, by the component managing device, the first components to implement the target operation instructions.

According to a seventh aspect of the present disclosure, a non-transitory computer readable medium, comprising at least one set of instructions, wherein when executed by at least one processor of a computing device, the at least one set of instructions causes the computing device to perform a method may be provided. The method may include obtaining exposure instructions including an exposure state of an imaging device; determining first components associated with the imaging device and one or more target operations of the first components corresponding to the exposure state; generating target operation instructions based on the one or more target operations of the first components; and controlling the first components to implement the target operation instructions is provided.

According to an eighth aspect of the present disclosure, a non-transitory computer readable medium, comprising at least one set of instructions, wherein when executed by at least one processor of a computing device, the at least one set of instructions causes the computing device to perform a method may be provided. The method may include obtaining exposure triggering parameters; determining an exposure state of an imaging device based on the exposure triggering parameters; generating exposure instructions including the determined exposure state; and transmitting the exposure instructions to first components for controlling the first components to perform one or more target operations corresponding to the exposure state.

According to a ninth aspect of the present disclosure, a non-transitory computer readable medium, comprising at least one set of instructions, wherein when executed by at least one processor of a computing device, the at least one set of instructions causes the computing device to perform a method may be provided. The method may include obtaining, by a master control device, exposure triggering parameters; determining, by the master control device, an exposure state of an imaging device based on the exposure triggering parameters; generating, by the master control device, exposure instructions including the determined exposure state; transmitting, by the master control device, the exposure instructions to a component managing device for controlling first components to perform one or more target operations corresponding to the exposure state; obtaining, by the component managing device, the exposure instructions of the exposure state; determining, by the component managing device, one or more target operations of the first components corresponding to the exposure state; generating, by the component managing device, target operation instructions based on the one or more target operations of the first components; and controlling, by the component managing device, the first components to implement the target operation instructions.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. These embodiments are non-limiting exemplary embodiments, in which like reference numerals represent similar structures throughout the several views of the drawings, and wherein.

DETAILED DESCRIPTION

The following description is presented to enable any person skilled in the art to make and use the present disclosure and is provided in the context of a particular application and its requirements. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but is to be accorded the widest scope consistent with the claims.

It will be understood that the term "system," "engine," "unit," "module," and/or "block" used herein are one method to distinguish different components, elements, parts, section or assembly of different level in ascending order. However, the terms may be displaced by another expression if they may achieve the same purpose.

Figure 2:
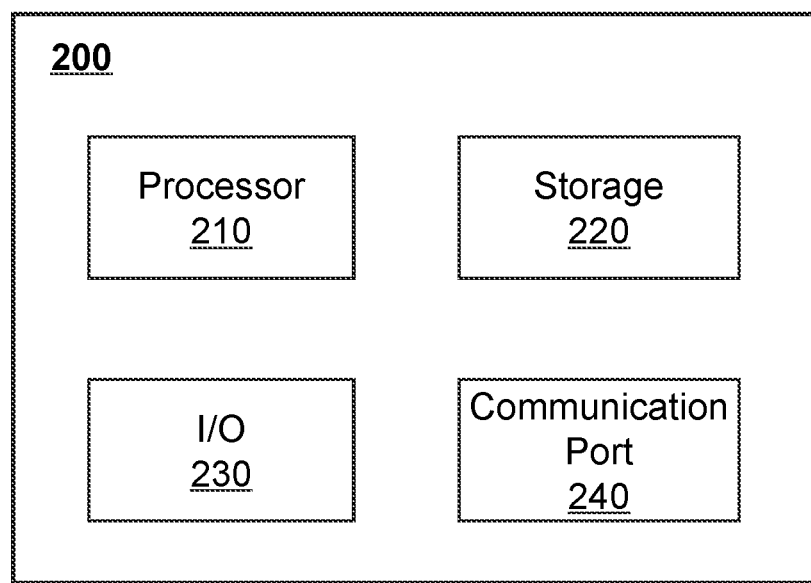
FIG. 2 is a schematic diagram illustrating hardware and/or software components of an exemplary computing apparatus 200 on which the control device 120 may be implemented according to some embodiments of the present disclosure.

Generally, the word "module," "unit," or "block," as used herein, refers to logic embodied in hardware or firmware, or to a collection of software instructions. A module, a unit, or a block described herein may be implemented as software and/or hardware and may be stored in any type of non-transitory computer-readable medium or another storage device. In some embodiments, a software module/unit/block may be compiled and linked into an executable program. It will be appreciated that software modules can be callable from other modules/units/blocks or from themselves, and/or may be invoked in response to detected events or interrupts. Software modules/units/blocks configured for execution on computing apparatus (e.g., processor 210 as illustrated in FIG. 2) may be provided on a computer-readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing apparatus, for execution by the computing apparatus. Software instructions may be embedded in firmware, such as an Erasable Programmable Read Only Memory (EPROM). It will be further appreciated that hardware modules/units/blocks may be included in connected logic components, such as gates and flip-flops, and/or can be included of programmable units, such as programmable gate arrays or processors. The modules/units/blocks or computing apparatus functionality described herein may be implemented as software modules/units/blocks, but may be represented in hardware or firmware. In general, the modules/units/blocks described herein refer to logical modules/units/blocks that may be combined with other modules/units/blocks or divided into sub-modules/sub-units/sub-blocks despite their physical organization or storage. The description may be applicable to a system, an engine, or a portion thereof.

The terminology used herein is for the purpose of describing particular example embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including," when used in this specification, specify the presence of stated features, integers, steps, operations, elements, and/or components, but do not preclude the presence or addition of one or more other features, integers, steps, operations, elements, components, and/or groups thereof.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

The flowcharts used in the present disclosure illustrate operations that systems implement according to some embodiments in the present disclosure. It is to be expressly understood, the operations of the flowchart may be implemented not in order. Conversely, the operations may be implemented in inverted order, or simultaneously. Moreover, one or more other operations may be added to the flowcharts. One or more operations may be removed from the flowcharts.

The present disclosure relates to methods and systems for radiation exposure process control. The radiation exposure process may be divided into at least one exposure state. The system may obtain exposure instructions including at least one exposure state, determine one or more target operations of components of an imaging device in each of the at least one exposure state, generate target operation instructions based on the one or more target operations of the components, and control the components to implement the target operation instructions.

According to an aspect of the present disclosure, a convenient way in which radiation exposure control functionality can be introduced into an existing imaging device without the need to modify the imaging system significantly may be provided. This is achieved by providing an insert system (e.g., the control device 120) coupled to a main system comprising a digital breast tomosynthesis (DBT), a full-field digital mammography (FFDM), a computed tomography (CT) device, a digital radiography (DR), and/or a computed radiography (CR) and supporting software of the insert system for installing on the main system.

Figure 1:
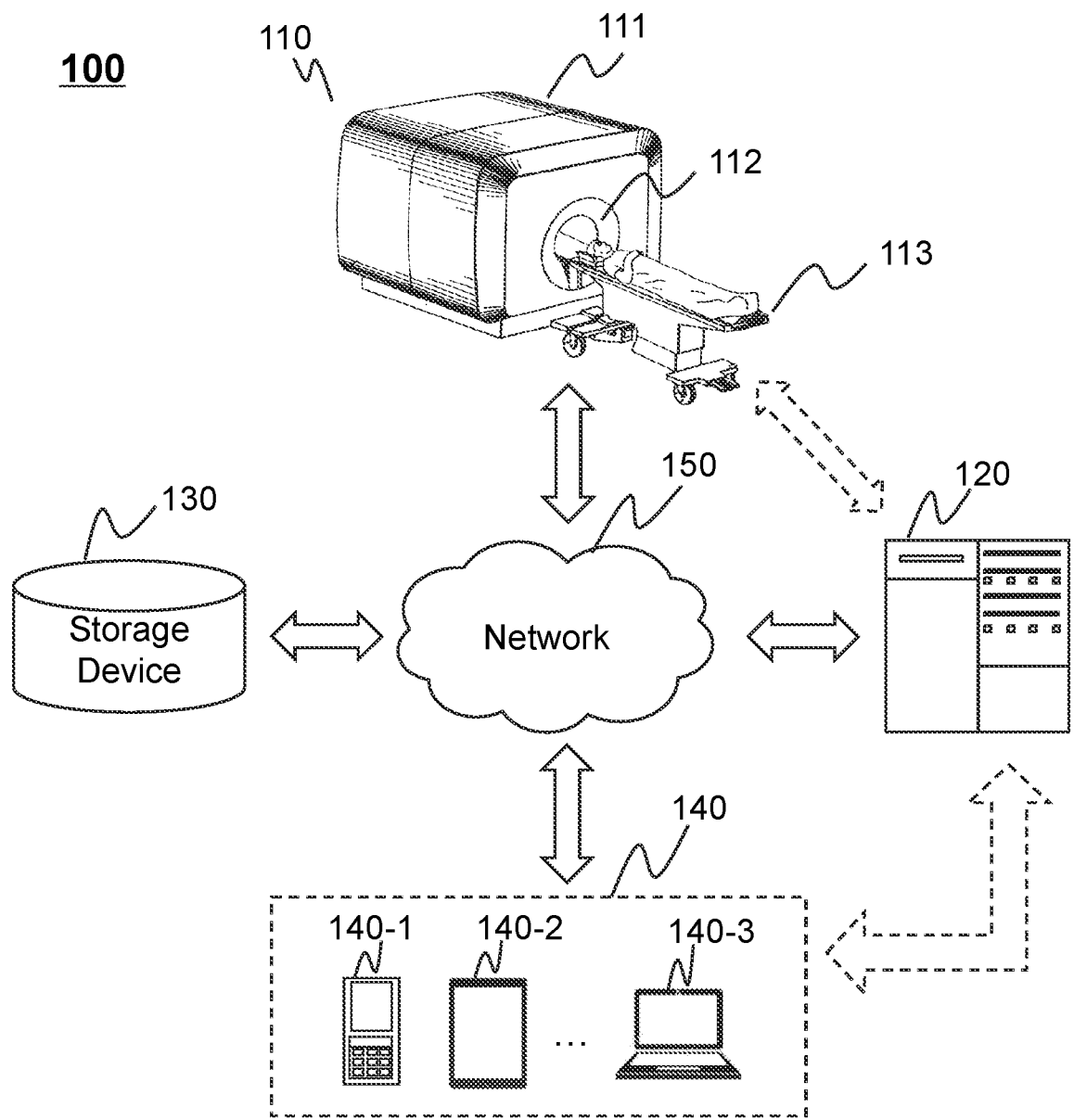
FIG. 1 is a schematic diagram illustrating an exemplary imaging system 100 according to some embodiments of the present disclosure.

FIG. 1 is a schematic diagram illustrating an exemplary imaging system 100 according to some embodiments of the present disclosure. As illustrated, the imaging system 100 may include an imaging scanner 110, a control device 120, a storage device 130, one or more terminals 140, and a network 150. The components in the imaging system 100 may be connected in various ways. Merely by way of example, as illustrated in FIG. 1, the imaging scanner 110 may be connected to the control device 120 through the network 150. As another example, the imaging scanner 110 may be connected with the control device 120 directly as indicated by the bi-directional arrow in dotted lines linking the imaging scanner 110 and the control device 120. As a further example, the storage device 130 may be connected with the control device 120 directly (not shown in FIG. 1) or through the network 150. As still a further example, one or more terminal(s) 140 may be connected with the control device 120 directly (as indicated by the bi-directional arrow in dotted lines linking the terminal(s) 140 and the control device 120) or through the network 150.

The imaging scanner 110 may scan a subject or a portion thereof that is located within its detection region, and generate imaging signals relating to the (part of) subject. In the present disclosure, the terms "subject" and "object" are used interchangeably. In some embodiments, the subject may include a body, a substance, or the like, or a combination thereof. In some embodiments, the subject may include a specific portion of a body, such as the head, the thorax, the abdomen, or the like, or a combination thereof. In some embodiments, the subject may include a specific organ, such as the breast, the heart, the esophagus, the trachea, the bronchus, the stomach, the gallbladder, the small intestine, the colon, the bladder, the ureter, the uterus, the fallopian tube, etc. In some embodiments, the imaging scanner 110 may include a DBT scanner, an FFDM scanner, a CT scanner, a DR scanner, a CR scanner, or the like. In some embodiment, the imaging scanner 110 may be a multi-modality device.

Merely for illustration purposes, a DBT scanner may be provided as an example for better understanding the imaging scanner 110, which is not intended to limit the scope of the present disclosure. The DBT scanner may include a gantry 111, a detecting region 112, and a scanning table 113. The gantry 111 may support one or more radiation sources and/or detectors (not shown). A subject (e.g., the breast of a patient) may be placed on the scanning table 114 for imaging scan. When the DBT scanner performs an imaging scan, a radiation exposure process (also referred to as exposure process) may be implemented involving a plurality of components (e.g., a flat-panel detector, a high-voltage generator, etc.). The plurality of components may perform a variety of operations to prepare for radiation exposure on the subject. In the radiation exposure, a radiation source may emit radioactive rays to the subject, and one or more detectors may detect radiation rays emitted from the detecting region 112. The radiation rays emitted from the detecting region 112 may be used to generate image data. The one or more detectors used may include, for example, a cesium iodide detector, a gas detector, etc.

The control device 120 may process data and/or information obtained and/or retrieve from the imaging scanner 110, the terminal(s) 140, the storage device 130 and/or other storage devices, and control the components, devices, modules, etc., of the imaging system 100. In some embodiments, the control device 120 may include a master control module (also referred to as master control device) and a component managing module (also referred to as component managing device). The master control module and/or the component managing module may process data and/or information, and generate control instructions to direct one or more components in the imaging system 100 to implement exemplary methods or operations in the present disclosure. For example, the master control device may determine an exposure state based on exposure triggering parameters, and generate exposure instructions of the determined exposure state. As another example, component managing device may determine components and one or more target operations of the components corresponding to the exposure state. In some embodiments, the control device 120 may be a single server or a server group. The server group may be centralized or distributed. In some embodiments, the control device 120 may be local or remote. For example, the control device 120 may access information and/or data stored in the imaging scanner 110, the terminal(s) 140, and/or the storage device 130 via the network 150. As another example, the control device 120 may be directly connected with the imaging scanner 110, the terminal(s) 140, and/or the storage device 130 to access stored information and/or data. In some embodiments, the control device 120 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof. In some embodiments, the control device 120 may be implemented on a computing apparatus 200 having one or more components illustrated in FIG. 2 in the present disclosure.

The storage device 130 may store data and/or instructions. In some embodiments, the storage device 130 may store data obtained from the terminal(s) 140 and/or the control device 120. For example, the storage device 130 may store data, images, algorithms, texts, instructions, program codes, etc.

In some embodiments, the storage device 130 may store data and/or instructions that the control device 120 may execute or use to perform exemplary methods described in the present disclosure. In some embodiments, the storage device 130 may include a mass storage device, a removable storage device, a volatile read-and-write memory, a read-only memory (ROM), or the like, or any combination thereof. Exemplary mass storage may include a magnetic disk, an optical disk, a solid-state drive, etc. Exemplary removable storage may include a flash drive, a floppy disk, an optical disk, a memory card, a zip disk, a magnetic tape, etc. Exemplary volatile read-and-write memories may include a random access memory (RAM). Exemplary RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. Exemplary ROM may include a mask ROM (MROM), a programmable ROM (PROM), an erasable programmable ROM (PEROM), an electrically erasable programmable ROM (EEPROM), a compact disk ROM (CD-ROM), and a digital versatile disk ROM, etc. In some embodiments, the storage device 130 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof.

In some embodiments, the storage device 130 may be connected with the network 150 to communicate with one or more components of the imaging system 100 (e.g., the control device 120, the terminal(s) 140, etc.). One or more components of the imaging system 100 may access the data or instructions stored in the storage device 130 via the network 150. In some embodiments, the storage device 130 may be directly connected with or communicate with one or more components of the imaging system 100 (e.g., the control device 120, the terminal(s) 140, etc.). In some embodiments, the storage device 130 may be part of the control device 120.

The terminal(s) 140 may include a mobile device 140-1, a tablet computer 140-2, a laptop computer 140-3, or the like, or any combination thereof. In some embodiments, the mobile device 140-1 may include a smart home device, a wearable device, a smart mobile device, a virtual reality device, an augmented reality device, or the like, or any combination thereof. In some embodiments, the smart home device may include a smart lighting device, a control device of an intelligent electrical apparatus, a smart monitoring device, a smart television, a smart video camera, an interphone, or the like, or any combination thereof. In some embodiments, the wearable device may include a smart bracelet, smart footgear, a pair of smart glasses, a smart helmet, a smartwatch, smart clothing, a smart backpack, a smart accessory, or the like, or any combination thereof. In some embodiments, the smart mobile device may include a smartphone, a personal digital assistant (PDA), a gaming device, a navigation device, a point of sale (POS) device, or the like, or any combination thereof. In some embodiments, the virtual reality device and/or the augmented reality device may include a virtual reality helmet, a virtual reality glass, a virtual reality patch, an augmented reality helmet, an augmented reality glass, an augmented reality patch, or the like, or any combination thereof. For example, the virtual reality device and/or the augmented reality device may include a Google Glass, an Oculus Rift, a Hololens, a Gear VR, etc. In some embodiments, the terminal(s) 140 may remotely operate the imaging scanner 110. In some embodiments, the terminal(s) 140 may operate the imaging scanner 110 via a wireless connection. In some embodiments, the terminal(s) 140 may receive information and/or instructions input by a user, and send the received information and/or instructions to the imaging scanner 110 or the control device 120 via the network 150. In some embodiments, the terminal(s) 140 may receive data and/or information from the control device 120. In some embodiments, the terminal(s) 140 may be part of the control device 120. In some embodiments, the terminal(s) 140 may be omitted.

In some embodiments, the terminal(s) 140 may send and/or receive information to the control device 120 via a user interface. The user interface may be in the form of an application for exposure control implemented on the terminal(s) 140. The user interface implemented on the terminal(s) 140 may be configured to facilitate communication between a user and the control device 120. In some embodiments, a user may input a request or an instruction via the user interface implemented on a terminal 140. The terminal(s) 140 may send the request or instruction to the control device 120 for controlling a radiation exposure as described elsewhere in the present disclosure (e.g., FIG. 6 and the descriptions thereof). In some embodiments, the user interface may facilitate the presentation or display of information and/or data (e.g., a signal, a parameter, etc) relating to exposure control received from the control device 120. In some embodiments, the information and/or data may be further configured to cause the terminal(s) 140 to display an image to the user.

The network 150 may include any suitable network that can facilitate the exchange of information and/or data for the imaging system 100. In some embodiments, one or more components of the imaging system 100 (e.g., the imaging scanner 110, the terminal(s) 140, the control device 120, or the storage device 130) may communicate information and/or data with one or more other components of the imaging system 100 via the network 150. In some embodiments, the network 150 may be any type of wired or wireless network, or a combination thereof. The network 150 may be and/or include a public network (e.g., the Internet), a private network (e.g., a local area network (LAN), a wide area network (WAN)), etc.), a wired network (e.g., an Ethernet network), a wireless network (e.g., an 802.11 network, a Wi-Fi network, etc.), a cellular network (e.g., a Long Term Evolution (LTE) network), a frame relay network, a virtual private network ("VPN"), a satellite network, a telephone network, routers, hubs, switches, server computers, and/or any combination thereof. Merely by way of example, the network 150 may include a cable network, a wireline network, a fiber-optic network, a telecommunications network, an intranet, a wireless local area network (WLAN), a metropolitan area network (MAN), a public telephone switched network (PSTN), a Bluetooth™ network, a ZigBee™ network, a near field communication (NFC) network, or the like, or any combination thereof. In some embodiments, the network 150 may include one or more network access points. For example, the network 150 may include wired and/or wireless network access points such as base stations and/or internet exchange points through which one or more components of the imaging system 100 may be connected with the network 150 to exchange data and/or information.

It should be noted that the above description of the imaging system 100 is merely provided for the purposes of illustration, not intended to limit the scope of the present disclosure. For persons having ordinary skills in the art, components contained in the storage management system 100 may be combined or adjusted in various ways, or connected with other components as sub-systems, and various variations and modifications may be conducted under the teaching of the present disclosure. However, those variations and modifications may not depart the spirit and scope of this disclosure. For example, the control device 120 may be a standalone device out of the imaging system 100, and the imaging system 100 may connect to the control device 120 via the network 150. All such modifications are within the protection scope of the present disclosure.

FIG. 2 is a schematic diagram illustrating hardware and/or software components of an exemplary computing apparatus 200 on which the control device 120 may be implemented according to some embodiments of the present disclosure. As illustrated in FIG. 2, the computing apparatus 200 may include a processor 210, a storage 220, an input/output (I/O) 230, and a communication port 240.

The processor 210 may execute computer instructions (program codes) and perform functions of the control device 120 in accordance with techniques described herein. The computer instructions may include, for example, routines, programs, objects, components, signals, data structures, procedures, modules, and functions, which perform particular functions described herein. For example, the processor 210 may process data obtained from the imaging scanner 110, the terminal(s) 140, the storage device 130, and/or any other component of the imaging system 100. Specifically, the processor 210 may process information of one or more components and generate control instructions (e.g., exposure instructions). In some embodiments, the exposure instructions may be stored in the storage device 130, the storage 220, etc. In some embodiments, the exposure instructions and/or one or more exposure states may be displayed on a display device by the I/O 230. In some embodiments, the processor 210 may perform instructions obtained from the terminal(s) 140. In some embodiments, the processor 210 may include one or more hardware processors, such as a microcontroller, a microprocessor, a reduced instruction set computer (RISC), an application specific integrated circuits (ASICs), an application-specific instruction-set processor (ASIP), a central processing unit (CPU), a graphics processing unit (GPU), a physics processing unit (PPU), a microcontroller unit, a digital signal processor (DSP), a field programmable gate array (FPGA), an advanced RISC machine (ARM), a programmable logic device (PLD), any circuit or processor capable of executing one or more functions, or the like, or any combinations thereof.

Merely for illustration, only one processor is described in the computing apparatus 200. However, it should be noted that the computing apparatus 200 in the present disclosure may also include multiple processors. Thus operations and/or method steps that are performed by one processor as described in the present disclosure may also be jointly or separately performed by the multiple processors. For example, if in the present disclosure the processor of the computing apparatus 200 executes both operation A and operation B, it should be understood that operation A and operation B may also be performed by two or more different processors jointly or separately in the computing apparatus 200 (e.g., a first processor executes operation A and a second processor executes operation B, or the first and second processors jointly execute operations A and B).

The storage 220 may store data/information obtained from the imaging scanner 110, the terminal(s) 140, the storage device 130, or any other component of the imaging system 100. In some embodiments, the storage 220 may include a mass storage device, a removable storage device, a volatile read-and-write memory, a read-only memory (ROM), or the like, or any combination thereof. For example, the mass storage may include a magnetic disk, an optical disk, a solid-state drive, etc. The removable storage may include a flash drive, a floppy disk, an optical disk, a memory card, a zip disk, a magnetic tape, etc. The volatile read-and-write memory may include a random access memory (RAM). The RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. The ROM may include a mask ROM (MROM), a programmable ROM (PROM), an erasable programmable ROM (PEROM), an electrically erasable programmable ROM (EEPROM), a compact disk ROM (CD-ROM), and a digital versatile disk ROM, etc. In some embodiments, the storage 220 may store one or more programs and/or instructions to perform exemplary methods described in the present disclosure. For example, the storage 220 may store a program for the control device 120 for controlling components (e.g., a flat-panel detector) to perform target operations in an exposure process according to one or more exposure states of the exposure process.

The I/O 230 may input or output signals, data, and/or information. In some embodiments, the I/O 230 may enable user interaction with the control device 120. In some embodiments, the I/O 230 may include an input device and an output device. Exemplary input devices may include a keyboard, a mouse, a touch screen, a microphone, or the like, or a combination thereof. Exemplary output devices may include a display device, a loudspeaker, a printer, a projector, or the like, or a combination thereof. Exemplary display devices may include a liquid crystal display (LCD), a light-emitting diode (LED)-based display, a flat-panel display, a curved screen, a television device, a cathode ray tube (CRT), or the like, or a combination thereof.

The communication port 240 may be connected with a network (e.g., the network 150) to facilitate data communications. The communication port 240 may establish connections between the control device 120 and the imaging scanner 110, the terminal(s) 140, or the storage device 130. The connection may be a wired connection, a wireless connection, or a combination of both that enables data transmission and reception. The wired connection may include an electrical cable, an optical cable, a telephone wire, or the like, or any combination thereof. The wireless connection may include Bluetooth, Wi-Fi, WiMax, WLAN, ZigBee, mobile network (e.g., 3G, 4G, 5G, etc.), or the like, or a combination thereof. In some embodiments, the communication port 240 may be a standardized communication port, such as RS232, RS485, etc. In some embodiments, the communication port 240 may be a specially designed communication port. For example, the communication port 240 may be designed in accordance with the digital imaging and communications in medicine (DICOM) protocol.

Figure 3:
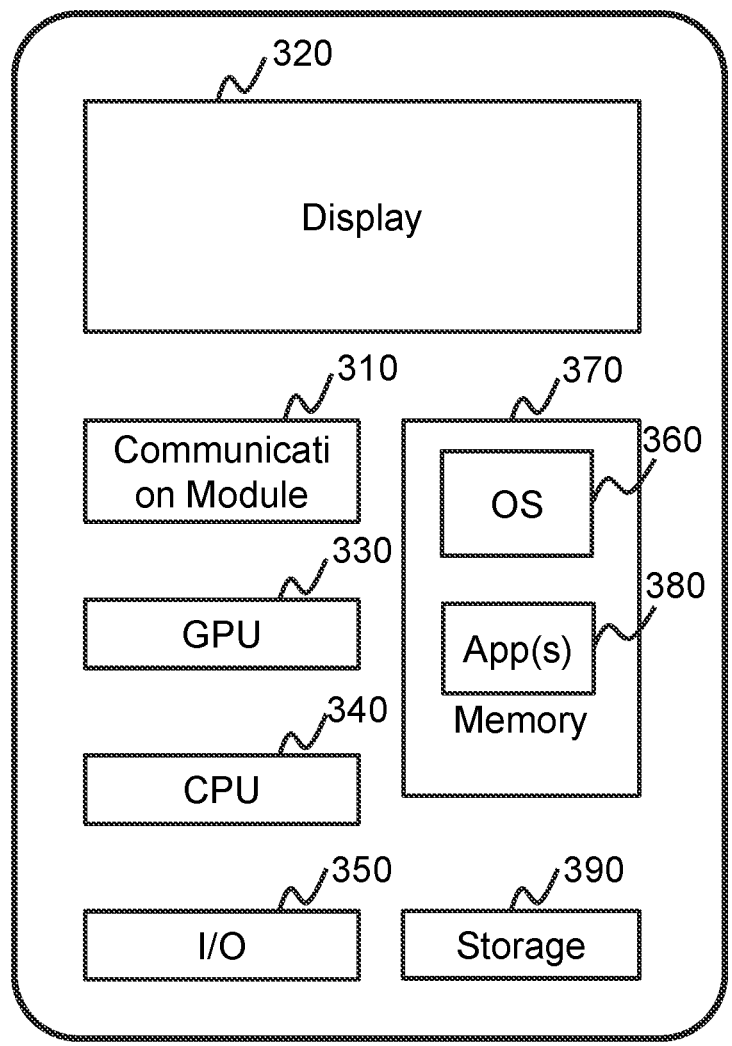
FIG. 3 is a schematic diagram illustrating hardware and/or software components of an exemplary mobile device 300 according to some embodiments of the present disclosure.

FIG. 3 is a schematic diagram illustrating hardware and/or software components of an exemplary mobile device 300 according to some embodiments of the present disclosure. As illustrated in FIG. 3, the mobile device 300 may include a communication platform 310, a display 320, a graphics processing unit (GPU) 330, a central processing unit (CPU) 340, an I/O 350, a memory 370, and a storage 390. In some embodiments, any other suitable component, including but not limited to a system bus or a controller (not shown), may also be included in the mobile device 300. In some embodiments, a mobile operating system 360 (e.g., iOS, Android, Windows Phone, etc.) and one or more applications 380 may be loaded into the memory 370 from the storage 390 in order to be executed by the CPU 340. The applications 380 may include a browser or any other suitable mobile apps for receiving and rendering information relating to imaging information processing or other information from the control device 120. User interactions with the information stream may be achieved via the I/O 350 and provided to the control device 120 and/or other components of the imaging system 100 via the network 150.

To implement various modules, units, and their functionalities described in the present disclosure, computer hardware platforms may be used as the hardware platform(s) for one or more of the elements described herein. The hardware elements, operating systems and programming languages of such computers are conventional in nature, and it is presumed that those skilled in the art are adequately familiar therewith to adapt those technologies to control an exposure process as described herein. A computer with user interface elements may be used to implement a personal computer (PC) or another type of work station or terminal device, although a computer may also act as a server if appropriately programmed. It is believed that those skilled in the art are familiar with the structure, programming and general operation of such computer equipment and as a result, the drawings should be self-explanatory.

Figure 4:
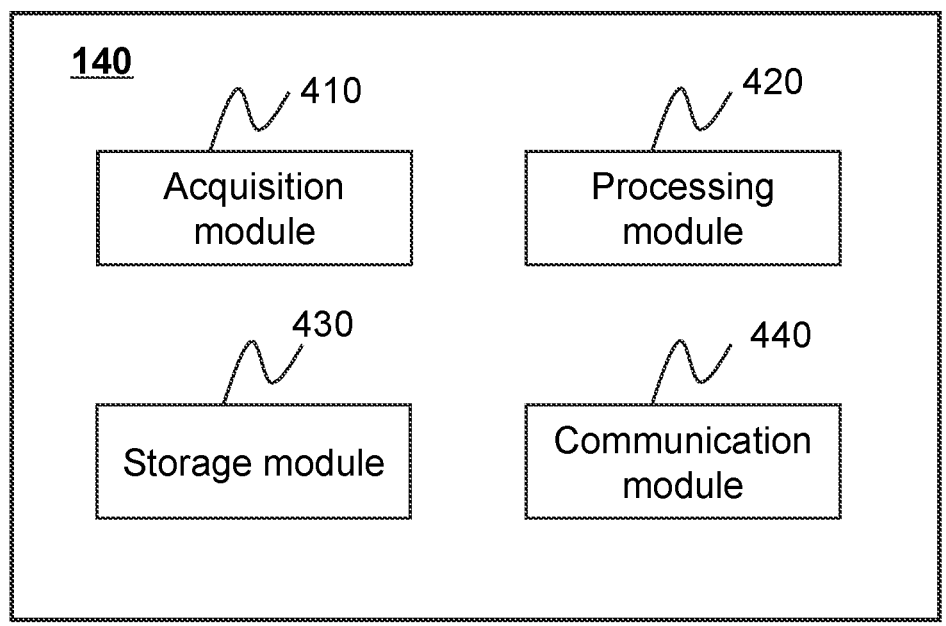
FIG. 4 is a block diagram illustrating an exemplary processing device according to some embodiments of the present disclosure.

FIG. 4 is a block diagram illustrating an exemplary control device according to some embodiments of the present disclosure. The control device 120 may include an obtaining module 410, a control module 420, an I/O module 430, and a communication module 440. One or more of the modules of the control device 120 may be interconnected. The connection(s) may be wireless or wired. At least a portion of the control device 120 may be implemented on a computing apparatus as illustrated in FIG. 2 or a mobile device as illustrated in FIG. 3.

The obtaining module 410 may obtain data, information, instructions, etc. For example, the obtaining module 410 may obtain state information of one or more components. The state information may be obtained after the components have performed operations with respect to a prior exposure state. As another example, the obtaining module 410 may obtain exposure instructions for controlling one or more components of the imaging system 100 (more specifically, the imaging scanner 110) to fulfill an exposure process. The exposure process may be divided into at least one exposure state, and each exposure state may correspond to a variety of operations of the components. The data, information, instructions, etc., may be acquired from the imaging scanner 110, the storage device 130, or any other storage device as described elsewhere in the present disclosure.

The control module 420 may process data and/or information, and/or generate control instruction for controlling one or more components (e.g., a flat-panel detector, a high-voltage generator, etc.) of the imaging system 100. The control module 420 may obtain data, information, and/or instructions from the obtaining module 410, the I/O module 430, and/or any storage devices capable of storing data (e.g., the storage device 130, or an external data source). Merely by ways of example, the control module 420 may determine an exposure state based on exposure triggering parameters, and generate exposure instructions of the determined exposure state. As another example, the control module 420 may determine components and one or more target operations of the components corresponding to the exposure state. As a further example, the control module 420 may generate target operation instructions based on the one or more target operations of the components, and control the components to implement the target operation instructions.

The control module 420 may include a hardware processor, such as a microcontroller, a microprocessor, a reduced instruction set computer (RISC), an application specific integrated circuits (ASICs), an application-specific instruction-set processor (ASIP), a central processing unit (CPU), a graphics processing unit (GPU), a physics processing unit (PPU), a microcontroller unit, a digital signal processor (DSP), a field programmable gate array (FPGA), an advanced RISC machine (ARM), a programmable logic device (PLD), any circuit or processor capable of executing one or more functions, or the like, or any combinations thereof.

The I/O module 430 may input or output signals, data or information. For example, the I/O module 430 may output an image to a user (e.g., a doctor, a patient, etc.). In some embodiments, the I/O module 430 may include an input device and an output device. Example input device may include a keyboard, a mouse, a touch screen, a microphone, or the like, or a combination thereof. Example output device may include a display device, a loudspeaker, a printer, a projector, or the like, or a combination thereof. Example display device may include a liquid crystal display (LCD), a light-emitting diode (LED)-based display, a flat-panel display, a curved screen, a television device, a cathode ray tube (CRT), or the like, or a combination thereof.

The communication module 440 may be connected to a network (e.g., the network 150) to facilitate data communications. The communication module 440 may establish connections between the control device 120, the storage device 130, and/or the one or more terminals 140. For example, the communication module 440 may send an image to the one or more terminals 140. The connection may be a wired connection, a wireless connection, any other communication connection that can enable data transmission and/or reception, and/or any combination of these connections. The wired connection may include, for example, an electrical cable, an optical cable, a telephone wire, or the like, or any combination thereof. The wireless connection may include, for example, a Bluetooth™ link, a Wi-Fi™ link, a WiMax™ link, a WLAN link, a ZigBee™ link, a mobile network link (e.g., 3G, 4G, 5G, etc.), or the like, or any combination thereof. In some embodiments, the communication module 440 may be and/or include a standardized communication port, such as RS232, RS485, etc. In some embodiments, the communication module 440 may be a specially designed communication port. For example, the communication module 440 may be designed in accordance with the digital imaging and communications in medicine (DICOM) protocol.

It should be noted that the above description of the control device 120 is merely provided for the purpose of illustration, and not intended to limit the scope of the present disclosure. For persons having ordinary skills in the art, various variations and modifications may be performed in the light of the present disclosure. However, those variations and modifications do not depart from the scope of the present disclosure. For example, one or more of the modules of the control device 120 mentioned above may be omitted or integrated into a single module. As another example, the control device 120 may include one or more additional modules, for example, a storage module for data storage.

Figure 5:
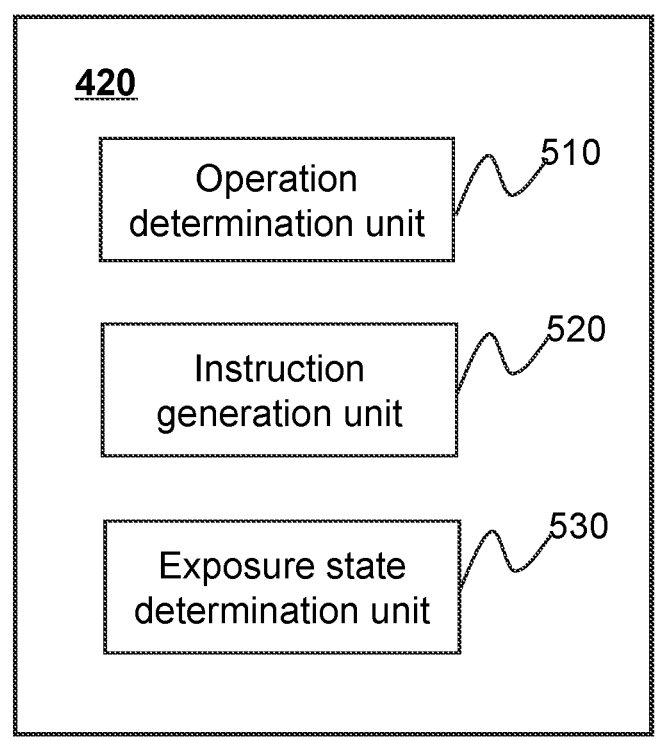
FIG. 5 is a block diagram illustrating an exemplary processing device according to some embodiments of the present disclosure.

FIG. 5 is a block diagram illustrating an exemplary control module according to some embodiments of the present disclosure. The control module 420 may include an operation determination unit 510, an instruction generation unit 520, and an exposure state determination unit 530.

The operation determination unit 510 may determine target operations of one or more components upon receiving exposure instructions. In some embodiments, operations of each component in the entire exposure process may be divided, according to the at exposure state, one or more phases, and each of the one or more phases may correspond to an exposure state. The operation determination unit 510 may establish a correspondence relationship between exposure states and operations of the components. Upon receiving the exposure instructions, the target operations that the components need to perform may be determined according to the correspondence relationship.

The instruction generation unit 520 may generate instructions for controlling one or more components. In some embodiments, the instruction generation unit 520 may generate target operation instructions based on one or more target operations of the components. The target operation instructions may be used to control the components to perform the target operations.

Merely by ways of example, When the instruction generation unit 520 associated with the flat-panel detector receives the "XRAYON" instruction, which represents the exposure start state, sent by the master control device, the instruction generation unit 520 may generate target operation instructions according to target operations corresponding to the "XRAYON" instruction so as to control the flat-panel detector to perform target operations including a window opening operation and a signal acquisition operation. If the current frame is not the last frame of an exposure sequence, a window closing operation may be performed after a signal acquisition operation is performed. Then the flat-panel detector may be controlled to perform a next open window preparation operation. If the current frame is the last frame of the exposure sequence, a window closing operation may be performed after a signal acquisition operation is performed. Then the flat-panel detector may be controlled to perform an image output operation.

In some embodiments, the instruction generation unit 520 may generate exposure instructions based on exposure states.

The exposure state determination unit 530 may determine exposure state of an imaging device (e.g., a DBT scanner). In some embodiments, exposure state determination unit 530 may determine the exposure state based on exposure triggering parameters. The exposure triggering parameters may include first parameters (also referred to as first triggering parameters) and second parameters (also referred to as second triggering parameters). The first parameters may be used to activate an exposure state of the imaging system 100, and second parameters representing state information of the components after the components have performed a prior exposure instruction.

It should be noted that the above description of the control module 420 is merely provided for the purpose of illustration, and not intended to limit the scope of the present disclosure. For persons having ordinary skills in the art, various variations and modifications may be performed in the light of the present disclosure. However, those variations and modifications do not depart from the scope of the present disclosure. For example, one or more of the units of the control module 420 mentioned above may be omitted or integrated into a single unit. As another example, the control module 420 may include one or more additional units, for example, an obtaining unit for data, information and/or instruction acquisition.

Figure 6:
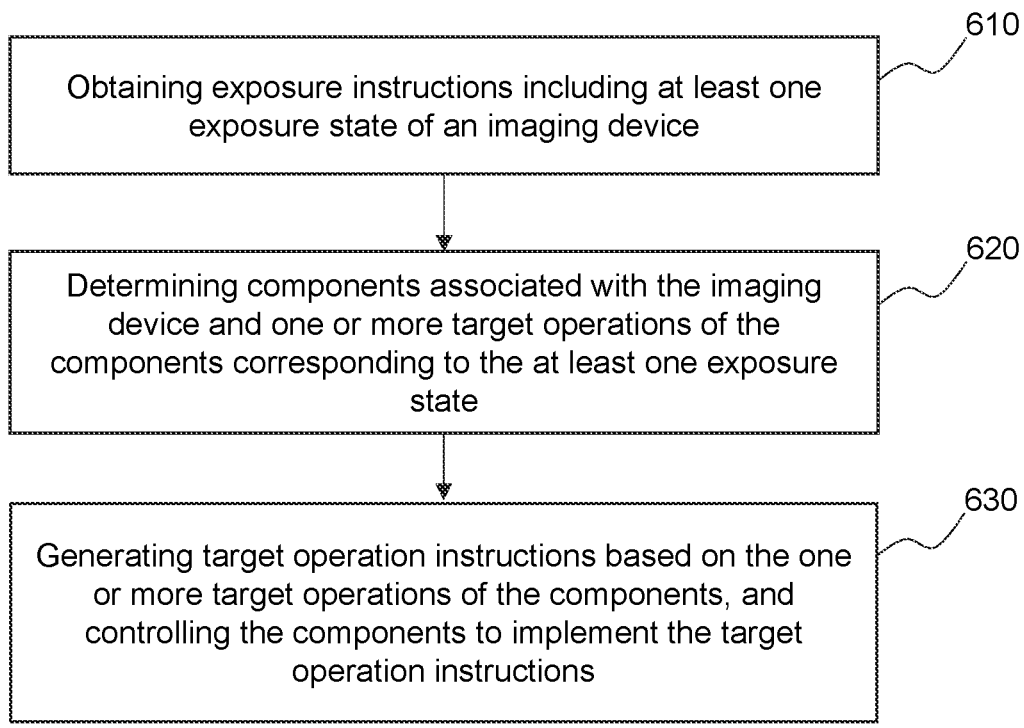
FIG. 6 is a flowchart of an exemplary process 600 for controlling a radiation exposure process according to some embodiments of the present disclosure.

FIG. 6 is a flowchart of an exemplary process 600 for controlling a radiation exposure process according to some embodiments of the present disclosure. The process 600 may be executed by the control device 120. For example, the process 600 may be implemented as a set of instructions (e.g., an application) stored in the storage, e.g., storage 220, the storage device 130, the storage 390, a storage device external to and accessible by the imaging system 100. The control device 120, the processor 210, and the CPU 340, may execute the set of instructions, and when executing the instructions, it may be configured to perform the process 600. The operations of the process 600 presented below are intended to be illustrative. In some embodiments, the process may be accomplished with one or more additional operations not described, and/or without one or more of the operations discussed. Additionally, the order in which the operations of the process 600 as illustrated in FIG. 6 and described below is not intended to be limiting. The process 600 may be applied to cases in which the component managing device controls multiple components to fulfill a radiation exposure process, and more particularly, to cases in which an apparatus for digital mammography is used for imaging between a plurality of imaging modes. Operations in the process 600 may be performed by an exposure process control device, which may be implemented entirely hardware, entirely software (including firmware, resident software, micro-code, etc.) or combining software and hardware implementation. For example, the exposure process control device may be configured as control device 120 or a part of the control device 120.

In 610, exposure instructions including at least one exposure state of an imaging device may be obtained.

In some embodiments, the obtaining module 410 may obtain exposure instructions for controlling one or more components of the imaging system 100 (more specifically, the imaging scanner 110) to fulfill an exposure process. The exposure process may be divided into at least one exposure state, and each exposure state may correspond to a variety of operations of the components.

In some embodiments, the imaging device may include a DBT scanner, an FFDM scanner, a CT scanner, a DR scanner, a CR scanner, or the like. A digital breast tomosynthesis (DBT) scanner may be taken as an example of the imaging device. A variety of imaging modes, such as MAMMO, TOMO, etc., may be incorporated in the DBT scanner. Exemplary imaging modes can include a manual single-shot mode (FFDM-Manual), an automatic single-shot mode (FFDM-AEC), a manual multi-shots mode (TOMO-Manual), an automatic multi-shots mode (TOMO-AEC), a manual combo-shots mode (Combo-Manual), an automatic combo-shots mode (Combo-AEC), or the like. Different imaging modes may correspond to different radiation exposure processes. For example, if the imaging mode is a single-shot mode, the imaging system 100 may control a plurality of components (e.g., flat-panel components) to shoot a single frame. The imaging system 100 may implement radiation exposure on a subject in an imaging mode relying on the components. If the imaging mode is a multi-shots mode, the imaging system 100 may control a plurality of components to shoot multiple frames, for example, by repeating operations in the single-shot mode.

In order to enable the imaging system 100 to implement multiple imaging modes, each imaging mode may be divided into several exposure states, and the exposure states may be implemented in control instructions (e.g., exposure instructions). The exposure instructions including the exposure states may be used to control the plurality of components to switch between the exposure states, fulfill the exposure process, and produce images.

The exposure states may correspond to a control process. Operations in the control process may be performed by the plurality of components so as to complete the exposure process, such that control processes of different exposure modes may be unified, and the imaging system 100 may be compatible with components of different types. In some embodiments, when components of different types are used, components currently used may be initialized according to models or types of the components, and a working mode and/or an exposure process suitable for the components may be determined, thus reducing workloads on data configuration, data backup, etc., in the updating or switching between components of different types, as well as lowering risks in the updating or switching.

When the master control device of the imaging system 100 sends exposure instructions including the at least one exposure state to the component managing device, the component managing device may determine operations to be performed by the components based on the received exposure instructions.

In some embodiments, the exposure states includes at least one of an exposure preparation state, an exposure start state, an exposure end state, and an idle state. The idle state refers that the components become idle after the exposure is fulfilled. In some embodiments, exposure instructions representing a corresponding exposure state may be preset (e.g., by a user, according to default settings of the imaging system 100, etc.) and/or encapsulated. Merely by ways of example, a PREPON instruction may represent the exposure preparation state, an XRAYON instruction may represent the exposure start state, an XRAYOFF instruction may represent the exposure end state, and a PREPOFF instruction may represent the idle state.

It should be noted that the received exposure instructions may include only one of the exposure states, or multiple exposure states that may be implemented sequentially, which is not limited in the present disclosure.

In 620, components associated with the imaging device and one or more target operations of the components corresponding to the at least one exposure state may be determined.

After the exposure instructions sent by the master control device are received, the component managing device may determine components and target operations that the components need to perform according to the at least one exposure state in the exposure instructions.

In some embodiments, before the target operations corresponding to the at least one exposure state are determined according to the exposure instructions, the component managing device may determine a correspondence relationship between exposure states and operations of the components, and determine the one or more target operations of the components corresponding to the at least one exposure state based on the correspondence relationship.

In some embodiments, a command interface between the components and the master control device of the imaging system 100 may be unified as exposure instructions including exposure states. A software control device associated with the components may need to pre-store target operations corresponding to the exposure instructions, such that the components may be controlled to perform the target operations once the exposure instructions are received.

Specifically, operations of each component in the entire exposure process may be divided, according to the at exposure state, one or more phases, and each of the one or more phases may correspond to an exposure state. Then a correspondence relationship between exposure states and operations of the components may be established. Upon receiving the exposure instructions, the target operations that the components need to perform may be determined according to the correspondence relationship.

Taking a flat-panel detector as an example, operations that need to be performed during an exposure process may include an open window preparation operation, a window opening operation, a signal acquisition operation, and an image output operation. The processing device 112 may match the operations to the exposure states so as to establish the correspondence relationship between exposure states and operations. For example, if the exposure state is the exposure preparation state, operations that the flat-panel detector needs to perform may include the open window preparation operation. If the exposure state is the exposure start state, operations that the flat-panel detector needs to perform may include the window opening operation, signal acquisition operation, image output operation, etc.

In 630, target operation instructions may be generated based on the one or more target operations of the components, and the components may be controlled to implement the target operation instructions.

In some embodiments, the component managing device may generate target operation instructions corresponding to the target operations that need to be performed according to a current exposure state, and the target operation instructions may be used to control the components to perform the target operations.

For example, when the software control device associated with the flat-panel detector receives the "XRAYON" instruction, which represents the exposure start state, sent by the master control device, the software control device may generate target operation instructions according to target operations corresponding to the "XRAYON" instruction so as to control the flat-panel detector to perform target operations including a window opening operation and a signal acquisition operation. If the current frame is not the last frame of an exposure sequence, a window closing operation may be performed after a signal acquisition operation is performed. Then the flat-panel detector may be controlled to perform a next open window preparation operation. If the current frame is the last frame of the exposure sequence, a window closing operation may be performed after a signal acquisition operation is performed. Then the flat-panel detector may be controlled to perform an image output operation.

The technical solution of the present disclosure provides a system and a method that receives exposure instructions including exposure states, rather than receives instructions of specific operations to be performed, such that the received instructions may be more concise and clear, and may reduce workloads of the master control device, thus reducing the complexity of the master control device. The system and method may also determine components associated with the imaging device and one or more target operations of the components corresponding to the at least one exposure state, generate target operation instructions based on the one or more target operations of the components, and control the components to implement the target operation instructions. In another word, the target operations corresponding to the at least one exposure state may be determined, then the components may be controlled to perform the target operations. In this way, the control of the exposure process may be unified into a control process of exposure states, such that the control of the exposure process may not change with types of the components, and the control of components of different types in the same imaging system may be realized without replacing software of the imaging system 100 When the components need to be changed or updated, code parameters of the component managing device may be changed or the component managing device may be updated, and core logic of the master control device may not need to be adjusted. The design of the imaging system 100 may be simplified and become more reasonable, the maintenance of the system software may be more reliable, and the components may be updated more conveniently.

In some embodiments, the exposure process may relate to a flat-panel detector and/or a high-voltage generator.

In general, the components of the imaging system 100 that involve in the exposure process may include a gantry, an X-ray generator, a beam limiting device, a flat-panel detector, a high-voltage generator, etc. The correspondence relationship between operations performed by the flat-panel detector and the high-voltage generator and the at least one exposure state may be clear. Therefore, the operations of the flat-panel detector and/or the high-voltage generator may be mapped to the at least one exposure state, and controlled through exposure instructions including the at least one exposure state. In some embodiments, exposure operations of other components may be controlled under the existing exposure process. It is also possible to classify the operations of other components, map the classified operations to operation instructions, and use the operation instructions to fulfill the exposure process of other components.

In some embodiments, when one or more new components (second components) of a certain type different from the original components (first components) are added into the imaging system 100 (e.g., the imaging scanner 110) to implement the exposure process together with the first components. The control device 120 may obtain information of second components. The information may include, for example, the type, the manufacturing model, operations of the second components, functions of the second components, etc. The control device 120 may determine an exposure process of the second components and operations of the second components in the exposure process based on the information of the second components. In some embodiments, the exposure process may be divided into one or more exposure states regarding the second components. The one or more exposure states regarding the second components may be the same as or similar to the exposure states regarding the first components. The control device 120 may identify one or more target operations of the second components corresponding to the exposure states regarding the second components by separating the operations of the second components in the exposure process according to the exposure states. Then the control device 120 may generate target operation instructions for controlling the second components to implement the one or more target operations.

Figure 7:
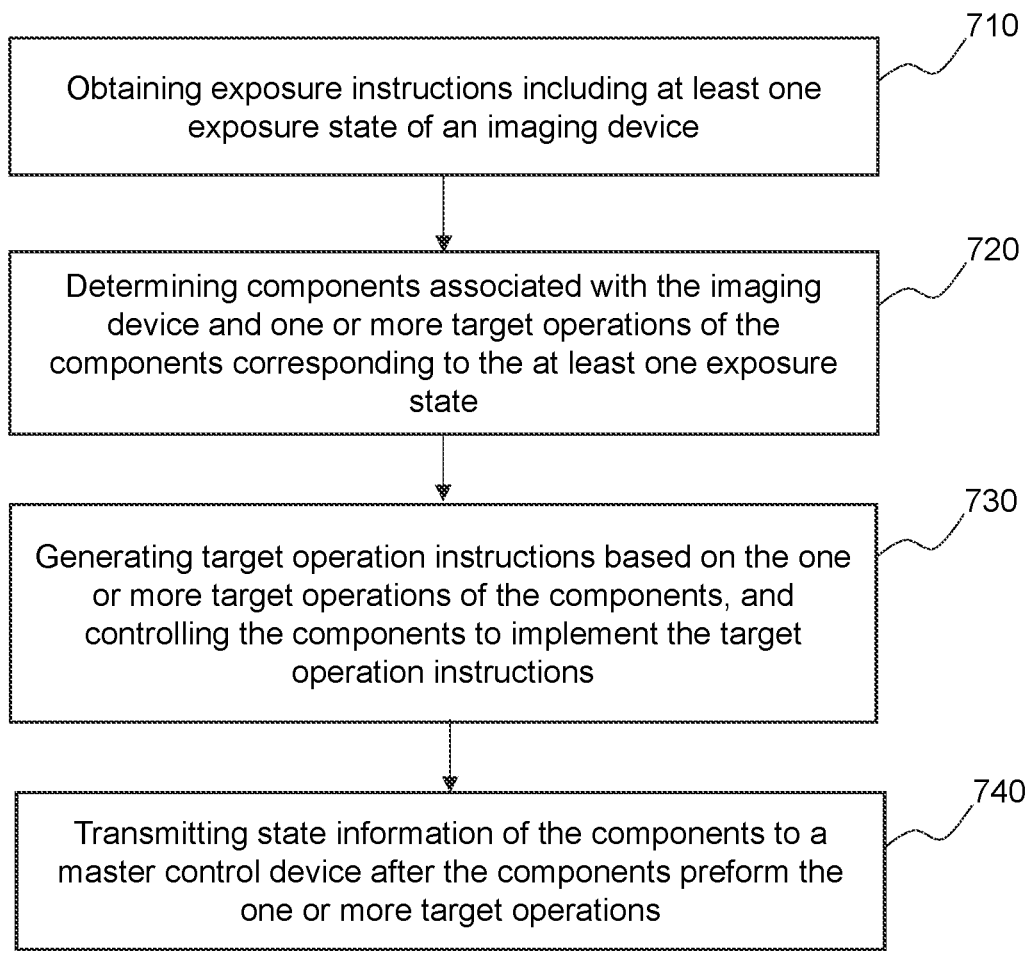
FIG. 7 is a flowchart of an exemplary process 700 for controlling a radiation exposure process according to some embodiments of the present disclosure.

FIG. 7 is a flowchart of an exemplary process 700 for controlling a radiation exposure process according to some embodiments of the present disclosure. The operations of the process 700 presented below are intended to be illustrative. In some embodiments, the process may be accomplished with one or more additional operations not described, and/or without one or more of the operations discussed. Additionally, the order in which the operations of the process 700 as illustrated in FIG. 7 and described below is not intended to be limiting.

In 710, the component managing device may obtain exposure instructions including at least one exposure state of an imaging device.

In 720, the component managing device may determine components associated with the imaging device and one or more target operations of the components corresponding to the at least one exposure state.

In 730, the component managing device may generate target operation instructions based on the one or more target operations of the components, and control the components to implement the target operation instructions.

In some embodiments, the operations in 710 through 730 may be the same as or similar to the operation in 610 through 630 in the process 600 as illustrated in FIG. 6.

In 740, the component managing device may transmit state information of the components to the master control device after the components preform the one or more target operations.

In some embodiments, in order to enable the master control device to determine whether to perform operations in a next step according to state information of each component, the state information of the components may be fed back to the master control device after the target operations are performed, such that the master control device may acquire an execution state of the current components. The execution state of the current components may include, for example, whether the target operations are executed successfully, whether there is a failure in the execution, etc. Further, the master control device may determine, according to the state information of the components, whether each component satisfies preset conditions for performing operations in the next step. If each component satisfies the preset conditions for performing the operations in the next step, exposure instructions including an exposure state corresponding to the operations in the next step may be sent to each component.

In some embodiments, state information identifiers may be preset, for example, by a user, according to default settings of the imaging system 100, etc. The state information identifiers may correspond to the state information of the components. When it is detected that the target operations are preformed, a state information identifier corresponding to the state information of the components may be sent to the master control device.

Taking the flat-panel detector as an example, the state information of the flat-panel detector may be defined as, for example, idle, exposure window preparation, exposure ready, exposure window open, image output, etc., and state information identifiers corresponding to the state information may be set. Table 1 shows a correspondence relationship between state information identifiers, state information, and operations of the flat-panel detector.

TABLE 1

| State information identifier | State information | Operations of flat-panel detector |
|---|---|---|
| IDLE | Idle | None |
| PREP | Exposure window preparation | Preparing for opening the window |
| READY | Exposure ready | None |
| EXPWIN_OPEN | Exposure window open | Opening the window and acquire signals |
| IMAGE_OUTPUT | Image output | Outputting images |

Correspondingly, the preset conditions for sending the exposure instructions are pre-stored in the master control device. Taking the flat-panel detector as an example, Table 2 shows a correspondence relationship between exposure instructions, exposure states, and preset conditions that the flat-panel detector needs to satisfy for sending the exposure instructions.

TABLE 2

| Exposure instruction | Exposure state | State of flat-panel detector |
|---|---|---|
| PREPON | Exposure preparation state | The flat-panel detector is in the READY state and the current frame is the first frame |
| XRAYON | Exposure start state | The flat-panel detector is in the EXPWIN_OPEN state |
| XRAYOFF | Exposure end state | The flat-panel detector is in the EXPWIN_OPEN state |
| PREPOFF | Idle state | The flat-panel detector is in the EXPWIN_CLOSE state |

Figure 8:
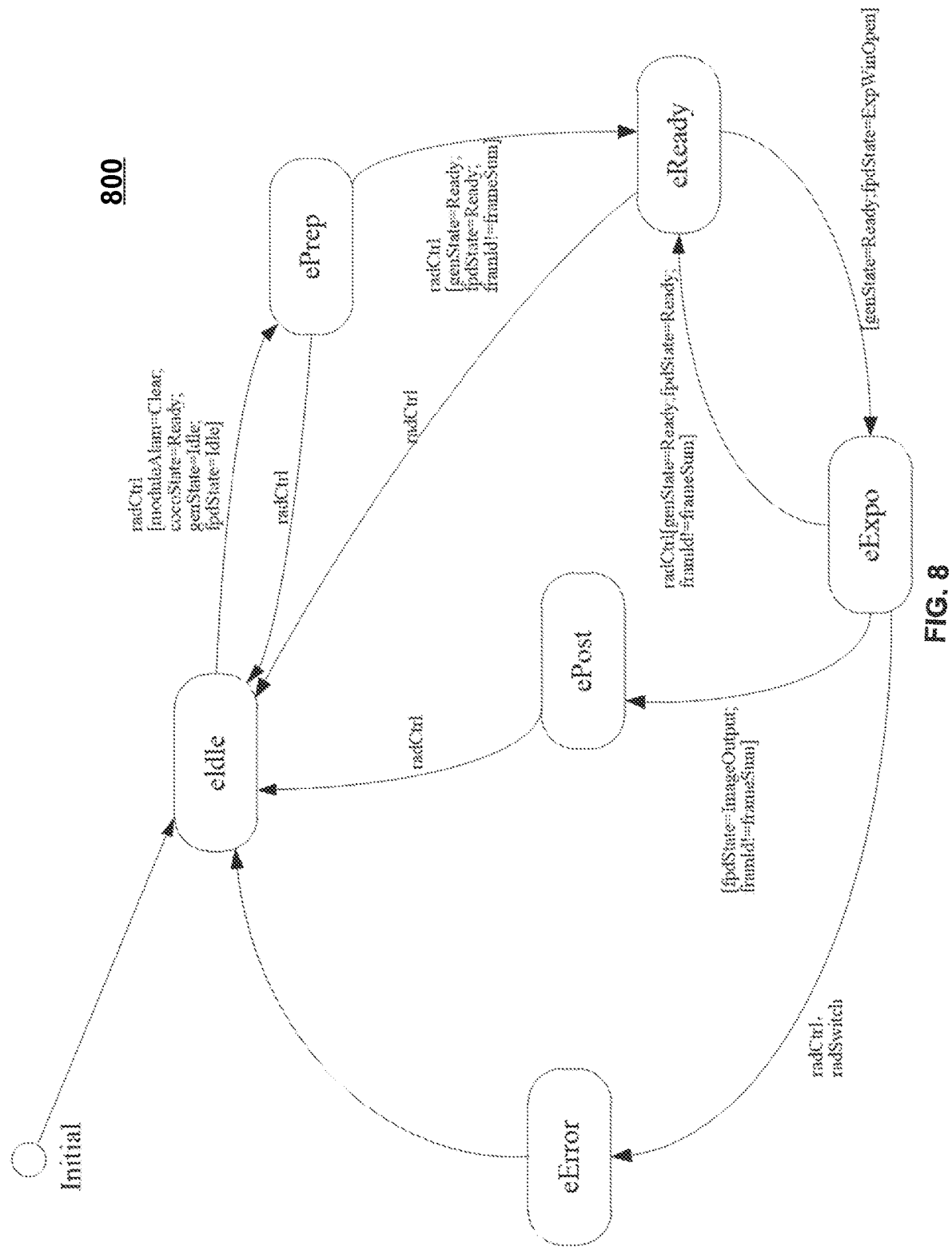
FIG. 8 is a schematic diagram illustrating a transition between exposure states of an exposure process according to some embodiments of the present disclosure.

FIG. 8 is a schematic diagram illustrating a transition between exposure states of an exposure process according to some embodiments of the present disclosure. Transition manners and conditions for transiting between exposure states of an exposure process of a flat-panel detector may be described for illustration purposes. The exposure process may include a plurality of exposure states. As shown in FIG. 8, the each bar in the figure represents an exposure state. For example, a bar labeled eIdle represents an idle state, a bar labeled ePrep represents an exposure preparation state, a bar labeled eReady represents an exposure ready state, a bar labeled eExpo represents an exposure window open state, a bar labeled ePost represents an image output state, and a bar labeled eError represents an error state. A direction of an arrow in the figure indicates a direction of a transition from one exposure state to another exposure state. Text being close to the arrow (such as [genState=Ready; fpdState=ExpWinOpen]) indicates preset conditions that need to be satisfied when the exposure process transits from an exposure state on one side of the arrow to another exposure state on the other side of the arrow. Merely for illustration purposes, preset conditions that need to be satisfied when the exposure process transits from the eReady state to the eExpo state may be that the high-voltage generator is in the exposure ready state and the flat-panel detector is in the exposure window open state. Merely for illustration purposes, the control of components, according to exposure instructions, in an exposure process may be described in combination with Table 1, Table 2, and FIG. 8 by taking a flat-panel detector controlled by a software control device associated with the flat-panel detector upon receiving exposure instructions sent by the master control device as an example.

In some embodiments, if the imaging mode is a multi-shots mode or a combination of single-shot and multi-shots mode, the exposure sequence may include multiple image frames. The master control device may determine an exposure process according to the imaging mode selected by a user, then send exposure instructions to the flat-panel detector according to the exposure process. When the master control device sends a PREPON instruction to the flat-panel detector, the software control module associated with the flat-panel detector may receive the instruction sent by the master control device, determine, according to the PREPON instruction, that the operation to be performed is the open window preparation operation, and control the flat-panel detector to perform the open window preparation operation.

If it is detected that the open window preparation operation of the flat-panel detector is performed, the flat-panel detector may enter into a exposure ready state, and the software control device associated with the flat-panel detector may sends the corresponding state information identifier "READY" to the master control device.

When the master control device receives the state information identifier "READY" sent by the software control device associated with the flat-panel detector and the current frame is the first frame of the exposure sequence, the imaging system 100 may determine that a preset condition related to the flat-panel detector for sending an XRAYON instruction is satisfied. And if preset conditions related to other components for sending the XRAYON instruction are also satisfied, the master control device may send the XRAYON instruction to the flat-panel detector. The software control device associated with the flat-panel detector may receive the instruction, and control the flat-panel detector to open the window and acquire signals according to the instruction. If it is detected that operations of the flat-panel detector are complete, the software control device associated with the flat-panel detector may determine a working state into which the flat-panel detector needs to enter according to a current frame in the exposure sequence. For example, if the current frame is the last frame of the exposure sequence, the flat-panel detector may be controlled to close the window and enter into the IMAGE OUTPUT state. Otherwise, the flat-panel detector may be controlled to return to the PREP state and a state information identifier corresponding to the PREP state may be sent to the master control device. The master control device may determine operation instructions in the next step according to the state information identifier and the exposure process corresponding to the imaging mode selected by the user. After the master control device receives the state information identifier IMAGE OUTPUT sent by the software control device associated with the flat-panel detector, the master control device may determine that the exposure process is complete.

When the master control device determines that the exposure process is complete, the master control device may send a PREPOFF instruction to the flat-panel detector. The software control device associated with the flat-panel detector may receive the instruction to control the panel detector to enter an idle state, and send the state information identifier "IDLE" corresponding to the idle state to the master control device.

The exposure control process may be described by taking a high-voltage generator as an example below. The working state of the high-voltage generator may be defined as an idle state, an exposure preparation state, an exposure ready state, and an exposure state. The four states may correspond to state information identifiers IDLE, PREP, READY and XRAYON, respectively. Table 3 shows a correspondence relationship between state information identifiers, state information, and operations of the high-voltage generator. Table 4 shows a correspondence relationship between exposure instructions, exposure states, and preset conditions that the high-voltage generator needs to satisfy for sending exposure instructions.

TABLE 3

| Working state | Description | Operations of high-voltage generator |
|---|---|---|
| IDLE | Idle | None |
| PREP | Exposure preparation | The anode of the tube start rotating |

TABLE 3-continued

| Working state | Description | Operations of high-voltage generator |
|---|---|---|
| READY | Exposure ready | None |
| XRAYON | Exposure start | After the exposure is complete, return to READY state or IDLE state according to exposure mode |

TABLE 4

| Exposure instruction | Exposure state | State of high-voltage generator |
|---|---|---|
| PREPON | exposure preparation state | The current frame is the first frame and the high-voltage generator is in the IDLE state |
| XRAYON | exposure start state | The high-voltage generator is in the READY state and the exposure is not complete |
| XRAYOFF | exposure end state | The high-voltage generator is in the XRAYON state |
| PREPOFF | idle state | The exposure is complete and the high-voltage generator is in the READY state |

Specifically, if the imaging mode is a multi-shots mode or a combination of single-shot and multi-shots mode, the exposure sequence may include multiple image frames. When the master control device receives the state information identifier "IDLE" sent by a high-voltage module associated with the high-voltage generator and the current frame is the first frame of the exposure sequence, it may be determined that the high-voltage generator satisfies the preset conditions for sending the PREPON instruction. If other components also satisfy the preset conditions for sending the PREPON instruction, the master control device may send the PREPON instruction to the high-voltage generator, and the high-voltage module associated with the high-voltage generator may receive the instruction and send a PREP signal so as to control the anode of the tube of the high-voltage generator to start to rotate.

When the master control device receives the state information identifier "READY" sent by the high-voltage module and does not receive an exposure completion signal (i.e., a signal indicating the completion of the exposure process), it may be determined that the high-voltage generator is ready for radiation exposure (i.e., the high-voltage generator is in the exposure ready state, and the radiation exposure is not complete), and the high-voltage generator satisfies the preset conditions for sending the XRAYON instruction. The master control device may send the XRAYON instruction to the high-voltage generator when other components also satisfy the preset conditions for sending the XRAYON instruction. When the high-voltage generator receives the XRAYON instruction sent by the master control device, the high-voltage module associated with the high-voltage generator may send an exposure signal (required for the first frame) and an automatic exposure control signal to the high-voltage generator so as to control the high-voltage generator to supply power to the tube, thereby controlling the tube to emit radioactive rays to a subject.

When the master control device receives the state information identifier XRAYON sent by the high-voltage module, the master control device may determine that the high-voltage generator is in the exposure state, and control the high-voltage module to send the automatic exposure control signal to the high-voltage generator so as to control the radiation exposure. When the radiation exposure on the subject is complete, the high-voltage generator may output the exposure completion signal, such that the master control device may receive the feedback of the completion of the radiation exposure from the high-voltage generator. Then if the master control device receives the state information identifier "READY" again from the high-voltage module, it may be determined that the high-voltage generator satisfies the preset conditions for sending the PREPOFF instruction. If other components also satisfy the preset conditions for sending the PREPOFF instruction, the master control device may sends the PREPOFF instruction to the high-voltage generator, and the high-voltage module associated with the high-voltage generator may control the high-voltage generator to enter the idle state via the exposure signal and the automatic exposure control signal.

The technical solutions of the present disclosure further provides an operation for transmitting state information of the components to the master control device after the components perform the one or more target operations. The master control device may determine whether to perform subsequent part of the exposure process according to the state information of the components, thus providing a more concise transition between exposure states in the exposure process.

Figure 9:
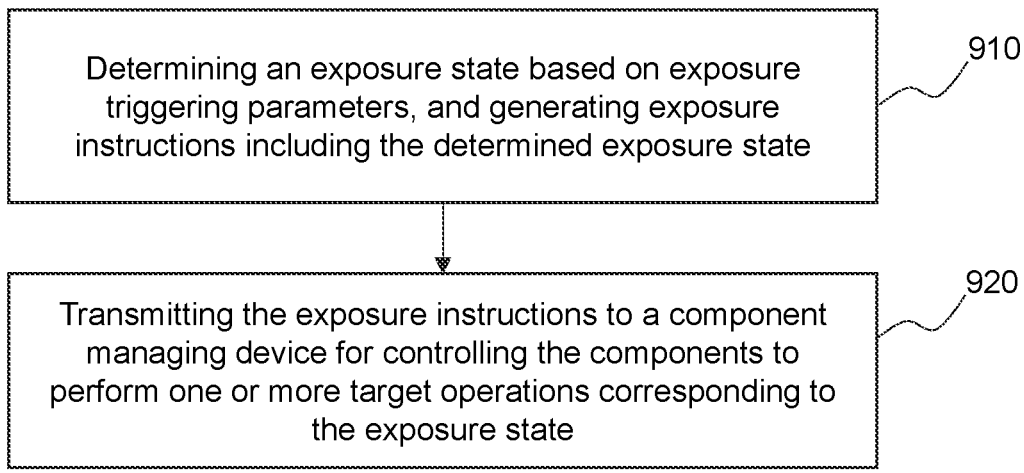
FIG. 9 is a flowchart of an exemplary process 900 for controlling a radiation exposure process according to some embodiments of the present disclosure.

FIG. 9 is a flowchart of an exemplary process 900 for controlling a radiation exposure process according to some embodiments of the present disclosure. The process 600 may be applied to cases in which the component managing device controls multiple components to fulfill a radiation exposure process, and more particularly, to cases in which an apparatus for digital mammography is used for imaging between a plurality of imaging modes. Operations in the process 600 may be performed by an exposure process control device, which may be implemented entirely hardware, entirely software (including firmware, resident software, micro-code, etc.) or combining software and hardware implementation. For example, the exposure process control device can be configured as control device 120 or a part of the control device 120.

In 910, an exposure state may be determined based on exposure triggering parameters, and exposure instructions including the determined exposure state may be generated.

In some embodiments, the exposure triggering parameters may include first parameters (also referred to as first triggering parameters) and second parameters (also referred to as second triggering parameters). The first parameters may be used to activate an exposure state of the imaging system 100, and second parameters representing state information of the components after the components have performed a prior exposure instruction.

In some embodiments, the master control device may generate exposure instructions according to the first parameters that triggers the initiation of an exposure state. In some embodiments, the first parameters may be input by a user, according to default settings of the imaging system 100, etc.

In some embodiments, the master control device may include a task execution module, and an exposure module (also referred to as an exposure operation execution module). The exposure module may further include a plurality of exposure sub-modules. The task execution module may store a list of imaging tasks (also referred to as tasks) and a correspondence relationship between tasks and exposure sub-modules. In some embodiments, a task may correspond to an exposure sub-module. The task execution module may determine an exposure sub-module corresponding to the task, for example, selected by the user, according to the correspondence relationship between tasks and exposure sub-modules. The exposure sub-module may store an exposure process corresponding to the task. For example, when a user selects a puncture positioning exposure task, the task execution module may determine an exposure sub-module corresponding to the puncture positioning exposure task (e.g., a puncture positioning exposure execution module), and complete a puncture positioning exposure process using the puncture positioning exposure execution module.

The control logic of the master control device may be clearer by dividing the master control device into the task execution module and the plurality of exposure sub-modules. In addition, if it is necessary to add a new task to existing tasks, an identifier of the task may be added into the task execution module, an exposure sub-module corresponding to the task may be added into the exposure module, and a correspondence relationship between the identifier of the task and the exposure sub-module of the task may be established in the service module. In this case, the core logic of the master control device may not need to be changed, thus simplifying the research and development (R&D) process of a new task, making the R&D of a new task more convenient, as well as increasing the stability of the master control device.

In some embodiments, when a user selects an imaging task, and initiate an imaging process, for example, by clicking a start button on a user interface through a terminal 140. The task execution module in the master control device may determine an exposure sub-module corresponding to the task according to the imaging task selected by the user. The exposure sub-module may determine an exposure state to be implemented based on first parameters triggered by the user and an exposure process pre-stored in the exposure sub-module, and generate exposure instructions including the exposure state. For example, after a user selects the puncture positioning exposure task and clicks a start button, the task execution module may determine a puncture positioning exposure execution module corresponding to the puncture positioning exposure task, determine an exposure state to be executed according to the exposure process pre-stored in the puncture positioning exposure execution module, and generate an corresponding exposure instruction. Merely by ways of example, if the puncture positioning exposure execution module determines that the exposure state to be implemented is the exposure preparation state, an exposure instruction including the exposure preparation state may be generated. The PREPON instruction may represent the exposure preparation state.

In some embodiments, the master control device may further generate an exposure instruction according to the second parameters representing state information of the components.

In some embodiments, during the exposure process, the exposure module in the master control device receives the state information of the components, and determines whether to perform operations in a next step (e.g., operations in a next exposure state) according to the state information of components. Specifically, if the state information of the components satisfy preset conditions for performing the operations in the next step, the exposure module may obtain second parameters representing the state information of the component, and determine the next exposure state (i.e., exposure state to be executed) according to the second parameters. For example, if the exposure module receives the state information of exposure ready fed back from each component, and a next exposure state to be implemented is exposure start state according to the stored exposure process, an exposure instruction including the exposure start state may be generated. The exposure start state may be represented using the XRAYON instruction.

In 920, the exposure instructions may be transmitted to the component managing device for controlling the components to perform one or more target operations corresponding to the exposure state.

The exposure instructions may be used to direct the component managing device to determine, according to the exposure state in the exposure instructions, target operations of the components corresponding to the exposure state.

In some embodiments, after the exposure instructions are generated, the master control device may send the exposure instructions to the component managing device, such that the component managing device may determine the target operations according to the exposure state in the exposure instructions, and generate target operation instructions to control the components to perform the target operations.

According to the technical solution described above, the exposure state may be determined according to the exposure triggering parameters, and exposure instructions including the exposure state may be generated and sent to the components. Instead of sending instructions of specific operations to be performed, the exposure instructions may be more concise and clear, and may reduce workloads of the master control device and reduce the complexity of the master control device. The exposure instructions may not change with imaging modes. Under a same imaging mode, exposure instructions may not change with type of the components, which realizes the control of components of different types in the imaging system without replacing the control software of the imaging system, thus making the design of the imaging system more simplified and reasonable, making software of the imaging system more reliable, as well as making the updating or replacement of the components much easier.

Figure 10:
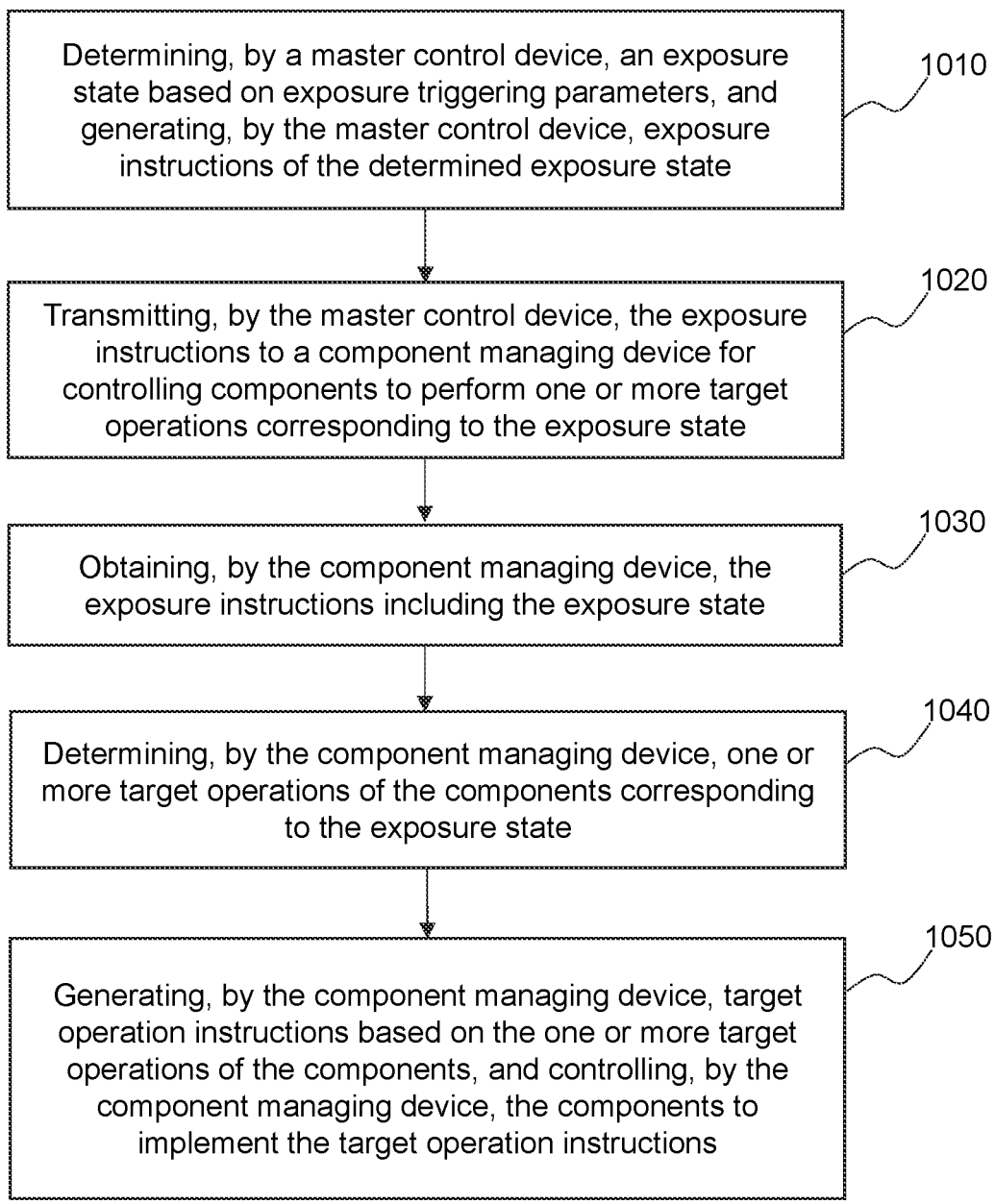
FIG. 10 is a flowchart of an exemplary process 1000 for controlling a radiation exposure process according to some embodiments of the present disclosure.

FIG. 10 is a flowchart of an exemplary process 1000 for controlling a radiation exposure process according to some embodiments of the present disclosure. The process 1000 may be applied to cases in which the component managing device controls multiple components to fulfill a radiation exposure process, and more particularly, to cases in which an apparatus for digital mammography is used for imaging between a plurality of imaging modes. Operations in the process 1000 may be performed by an exposure process control device, which may be implemented entirely hardware, entirely software (including firmware, resident software, micro-code, etc.) or combining software and hardware implementation. For example, the exposure process control device may be configured as the control device 120a part of the control device 120.

In 1010, the master control device may determine an exposure state based on exposure triggering parameters, and generate exposure instructions of the determined exposure state.

In 1020, the master control device may transmit the exposure instructions to a component managing device for controlling a plurality of components to perform one or more target operations corresponding to the exposure state.

In 1030, the component managing device may obtain the exposure instructions including the exposure state.

In 1040, the component managing device may determine components and one or more target operations of the components corresponding to the exposure state.

In 1050, the component managing device may generate target operation instructions based on the one or more target operations of the components, and control the components to implement the target operation instructions.

In some embodiment, the master control device may generate and send exposure instructions, and the component managing device may direct the components to perform target operations according to the exposure instructions. In some embodiments, the operations in 1010 and 1020 may be the same as or similar to the operations in 910 and 920 in the process 900, respectively. And the operations in 1030 through 1050 may be the same as or similar to the operations in 610 and 630 in the process 600.

The technical solution describe above provides that the master control device may determine an exposure state based on exposure triggering parameters, generate exposure instructions of the determined exposure state, and transmit the exposure instructions, rather than instructions of specific operations, to the component managing device for controlling a plurality of components to perform one or more target operations corresponding to the exposure state. The component managing device may obtain the exposure instructions including the exposure state, determine components and one or more target operations of the components corresponding to the exposure state, generate target operation instructions based on the one or more target operations of the components, and control the components to implement the target operation instructions. In this case, the instructions interacting between the master control device and the component managing device may be unified, which makes the instructions more concise and clear, reduces workloads of the master control device, and reduces the complexity of the master control device. The exposure instruction may not need to be changed with imaging modes. And the exposure instruction may not need to be changed with types of the components in a same imaging mode either. It realizes the control of components of different types in the imaging system without replacing the control software of the imaging system, thus making the design of the imaging system more simplified and reasonable, making software of the imaging system more reliable, as well as making the updating or replacement of the components much easier.

Figure 11:
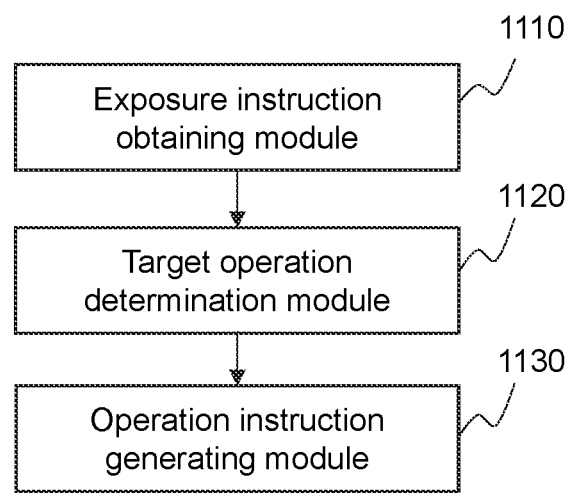
FIG. 11 is a block diagram of an exemplary exposure process control device according to some embodiments of the present disclosure.

FIG. 11 is a block diagram of an exemplary exposure process control device according to some embodiments of the present disclosure. The exposure flow control device may be implemented entirely hardware, entirely software (including firmware, resident software, micro-code, etc.) or combining software and hardware implementation. For example, the exposure process control device may be configured as the control device 120 or a part of the control device 120. As shown in FIG. 11, the exposure process control device may include an exposure instruction obtaining module 1110, a target operation determining module 1120, and an operation instruction generating module 1130.

The exposure instruction obtaining module 1110 may obtain exposure instructions including at least one exposure state. The target operation determining module 1120 may determine, according to the at least one exposure state in the exposure instructions, one or more target operations of a plurality of components. The operation instruction generating module 1130 may generate target operation instructions based on the one or more target operations of the components so as to control the components to implement the target operation instructions.

The technical solution of the present disclosure described above may provide more concise and clear instructions, reduce workloads of the master control device, and lower the complexity of the master control device by obtaining exposure instructions including exposure states, rather than instructions of specific operations to be performed by the components. Further, components and one or more target operations of the components corresponding to the exposure states may be determined, target operation instructions may be generated based on the one or more target operations of the components, and the components may be controlled to implement the target operation instructions. In another word, after the target operations corresponding to the exposure states are determined, the components may be controlled to perform the target operations, such that the control of the exposure process may not change with types of the components, and the control of components of different types in the same imaging system may be realized without replacing software of the imaging system 100 When the components need to be changed or updated, code parameters of the component managing device may be changed or the component managing device may be updated, and core logic of the master control device may not need to be adjusted. The design of the imaging system 100 may be simplified and become more reasonable, the maintenance of the system software may be more reliable, and the components may be updated more conveniently.

In some embodiments, the exposure process control device may further include a state information feedback module and a correspondence relationship establishing module (not shown in the figure).

The state information feedback module may send the state information of the components to the master control device when it is detected that the one or more target operations are complete.

The correspondence relationship establishing module may pre-establish a correspondence relationship between exposure states and operations of the components before the target operations corresponding to the exposure state are determined according to the exposure state in the exposure instruction. The correspondence relationship establishing module may determine the target operations of the components corresponding to the exposure state according to the correspondence relationship.

In some embodiments, the exposure states may include at least one of an exposure preparation state, an exposure start state, an exposure end state, and an idle state.

In some embodiments, the target operation determining module 1120 may determine, according to the exposure state in the exposure instruction, the target operations corresponding to the exposure state. The components may include a flat-panel detector and/or a high-voltage generator.

The exposure process control device provided according to some embodiments of the present disclosure may execute any exposure process control method provided in the processes 600, 700, etc., and may have modules implementing the methods (e.g., the methods provided in the processes 600, 700, etc.) and beneficial effects described above.

Figure 12:
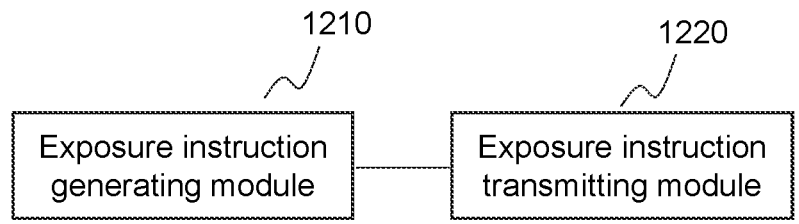
FIG. 12 is a block diagram of an exemplary exposure process control device according to some embodiments of the present disclosure.

FIG. 12 is a block diagram of an exemplary exposure process control device according to some embodiments of the present disclosure. The exposure flow control device may be implemented entirely hardware, entirely software (including firmware, resident software, micro-code, etc.) or combining software and hardware implementation. For example, the exposure process control device may be configured as the control device 120 or a part of the control device 120. As shown in FIG. 12, the exposure process control device may include an exposure instruction generating module 1210 and an exposure instruction transmitting module 1220.

The exposure instruction generating module 1210 may determine a current exposure state according to exposure triggering parameters, and generate exposure instructions including the exposure state. The exposure triggering parameters may include first parameters for activating the exposure state and second parameters representing state information of the components after the components have performed a prior exposure instruction.

The exposure instruction transmitting module 1220 may transmit the exposure instructions to the components. The exposure instructions may be used to instruct the components to determine, according to the exposure state in the exposure instructions, target operations corresponding to the exposure state of the components.

The technical solution describe above provides an exposure instruction generating module 1210 that may determine an exposure state based on exposure triggering parameters, and generate exposure instructions of the determined exposure state, and an exposure instruction transmitting module that may transmit the exposure instructions, rather than instructions of specific operations, to the component managing device for controlling a plurality of components to perform one or more target operations corresponding to the exposure state, which makes the instructions more concise and clear, reduces workloads of the master control device, and reduces the complexity of the master control device. The exposure instruction may not need to be changed with imaging modes. And the exposure instruction may not need to be changed with types of the components in a same imaging mode either. It realizes the control of components of different types in the imaging system without replacing the control software of the imaging system, thus making the design of the imaging system more simplified and reasonable, making software of the imaging system more reliable, as well as making the updating or replacement of the components much easier.

The exposure process control device provided according to some embodiments of the present disclosure may execute any exposure process control method provided in, for example, the process 900, and may have modules implementing the methods (e.g., the methods provided in the process 900) and beneficial effects described above.

Figure 13:
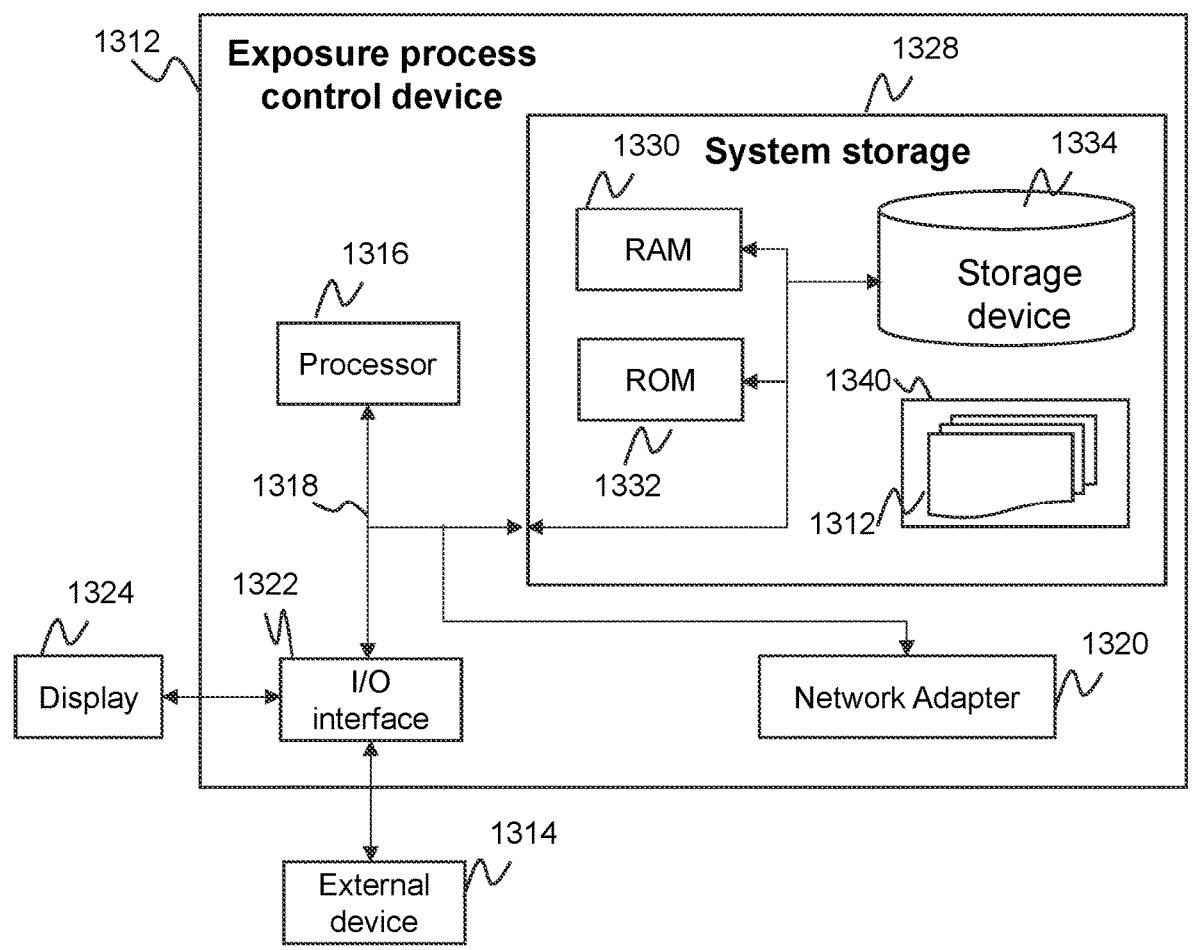
FIG. 13 is a schematic diagram of an exemplary exposure process control device 1312 according to some embodiments of the present disclosure.

FIG. 13 is a schematic diagram of an exemplary exposure process control device 1312 according to some embodiments of the present disclosure. The exposure process control device 1312 illustrated in FIG. 13 is merely an example, but not intended to limit the scope of the present disclosure.

As shown in FIG. 13, the exposure process control device 1312 may be or include a flat-panel detector, a high-voltage generator, etc. In some embodiments, the exposure process control device 1312 may be implemented by a general purpose computing device. The exposure process control device 1312 may include but are not limited to one or more processors 1316, a system memory 1328, and a bus 1318 that connects elements or components of the exposure process control device 1312, such as the system memory 1328, the one or more processors 1316, etc.

The bus 1318 may represent one or more of several types of bus structures, including a memory bus, a memory controller, peripheral bus, an accelerated graphics port, the one or more processors 1316, or a local bus using any of a variety of bus structures. For example, the bus structures may include but not limited to, an Industry Standard Architecture (ISA) bus, a Micro Channel Architecture (MAC) bus, an Enhanced ISA Bus, a Video Electronics Standards Association (VESA) local bus, a peripheral component interconnects (PCI) bus, etc.

The exposure process control device 1312 may include a variety of computer readable media. The computer readable media may be any available media including volatile or non-volatile media, removable or non-removable media, etc., that may be accessible by the exposure process control device 1312.

The system memory 1328 can include computer readable media in a form of volatile memory, for example, a random access memory (RAM) 1330 and/or a read-only memory (ROM) 1332. The exposure process control device 1312 may further include other removable/non-removable or volatile/non-volatile computer system storage media. Merely by ways of example, a storage device 1334 may be non-removable, non-volatile magnetic media (not shown in the figure, commonly referred to as a "hard disk drive") for reading and writing. Although not shown in FIG. 13, a disk drive for reading and writing to a removable non-volatile disk (such as a "floppy disk") and a removable non-volatile disk (such as a CD-ROM, a DVD-ROM, or other optical media) may be provided. In these cases, each drive may be coupled to the bus 1318 via one or more data medium ports. The system memory 1328 may include at least one program product having a set (e.g., at least one) of program modules configured to implement the functions provided in the above embodiments of the present disclosure.

A program/utility tool 1340 having a set (at least one) of program modules 1342, which may be stored, for example, in the memory 1328. The program modules 1342 may include but not limited to, an operating system, one or more applications, other program modules, or program data. Each or a combination of one or more of the above listed program modules may have a network environment implementation. The program module 1342 may perform the functions and/or methods provided in the described embodiments of the present disclosure.

The exposure process control device 1312 may also be in communication with one or more external devices 1314 (e.g., a keyboard, a pointing device, a display 1324, etc.), one or more devices that enable a user to interact with the exposure process control device 1312, and/or any devices (e.g., a network card, a modem, etc.) that enable the exposure process control device 1312 to communicate with one or more other computing devices. The communication may be realized via an input/output (I/O) interface 1322. Also, the exposure process control device 1312 may also communicate with one or more networks (e.g., a local area network (LAN), a wide area network (WAN), and/or a public network, such as the Internet) through a network adapter 1320. As shown in the figure, the network adapter 1320 may communicate with other modules of exposure process control device 1312 via the bus 1318. It should be understood that, other hardware and/or software modules may be utilized in combination with the exposure process control device 1312, including but not limited to microcode, device drivers, redundant processing units, external disk drive arrays, RAID systems, Tape drives, or data backup storage systems.

The one or more processors 1316 may implement, by running a program stored in the system memory 1328, various functional applications and/or data processing, for example, an exposure process control method provided in some embodiments of the present disclosure. The exposure process control method may include obtaining exposure instructions including at least one exposure state of an imaging device, determining components associated with the imaging device and one or more target operations of the components corresponding to the at least one exposure state, and generating target operation instructions based on the one or more target operations of the components, and controlling the components to implement the target operation instructions. The exposure process control method may further include determining an exposure state based on exposure triggering parameters, generating exposure instructions including the determined exposure state, and transmitting the exposure instructions to a component managing device for controlling the components to perform one or more target operations corresponding to the exposure state.

Those skilled in the art may understand that the one or more processors 1316 may also implement technical solutions of the exposure process control method provided by any embodiments of the present disclosure.

According to some embodiments of the present disclosure, a computer readable storage medium may be provided that stores a computer program, which is executed by a processor to implement an exposure process control method provided by various embodiments of the present disclosure. The exposure process control method may include obtaining exposure instructions including at least one exposure state of an imaging device, determining components associated with the imaging device and one or more target operations of the components corresponding to the at least one exposure state, and generating target operation instructions based on the one or more target operations of the components, and controlling the components to implement the target operation instructions. The exposure process control method may further include determining an exposure state based on exposure triggering parameters, generating exposure instructions including the determined exposure state, and transmitting the exposure instructions to a component managing device for controlling the components to perform one or more target operations corresponding to the exposure state.

As for the computer readable storage medium provided in some embodiments of the present disclosure, computer programs stored thereon may not be limited to the methods or operations as described above, and may also include any exposure process control methods provided in any embodiments of the present disclosure.

The computer readable storage medium of the present disclosure may include any combination of one or more computer readable media. The one or more computer readable media may be a computer readable signal medium or a computer readable storage medium. The computer readable storage medium may include but not limited to, an electronic, magnetic, optical, electromagnetic, infrared, or semiconductor system, apparatus, or device, or any combination thereof. More specific examples (non-exhaustive lists) of the computer readable storage media may include a portable computer disk with electrical connections having one or more wires, a hard disk, a random access memory (RAM), a read only memory (ROM), an erasable programmable read only memory (EPROM or flash memory), an optical fiber, a portable compact disk read only memory (CD-ROM), an optical storage device, a magnetic storage device, or any suitable combination of thereof. In some embodiments, a computer readable storage medium can be any tangible medium that may contain or store a program, which can be used by or in connection with an instruction execution system, apparatus or device.

The computer readable signal medium may store a data signal that is in a baseband or transmitted as part of a carrier wave, including computer readable program codes. Such data signals may take a variety of forms including but not limited to, electromagnetic signals, optical signals, or any suitable combination of thereof. The computer readable signal medium may also be any computer readable medium other than a computer readable storage medium, which can transmit, propagate, or transmit a program used by or in connection with an instruction execution system, apparatus, or device.

The program codes embodied on a computer readable storage medium may be transmitted by any suitable medium including but not limited to, wireless, wire, fiber optic cables, radio frequency (RF), etc., or any suitable combination thereof.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "unit," "module," or "system." Furthermore, aspects of the present disclosure may take the form of a computer program product embodied in one or more computer readable media having computer readable program code embodied thereon.

A computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C#, VB. NET, Python or the like, conventional procedural programming languages, such as the "C" programming language, Visual Basic, Fortran 2103, Perl, COBOL 2102, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, e.g., an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various inventive embodiments. This method of disclosure, however, is not to be interpreted as reflecting an intention that the claimed subject matter requires more features than are expressly recited in each claim. Rather, inventive embodiments lie in less than all features of a single foregoing disclosed embodiment.

In some embodiments, the numbers expressing quantities or properties used to describe and claim certain embodiments of the application are to be understood as being modified in some instances by the term "about," "approximate," or "substantially." For example, "about," "approximate," or "substantially" may indicate ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

We claim:

1. A system, comprising:
    at least one storage storing a set of instructions; and
    at least one processor configured to communicate with the at least one storage-, wherein when executing the set of instructions, the at least one processor is directed to perform operations including:
    obtaining exposure instructions including at least one exposure state of an imaging device;
    determining first components associated with the imaging device and one or more target operations of the first components corresponding to the at least one exposure state of the exposure instructions, wherein the first components include a flat-panel detector, the at least one exposure state includes at least one of an exposure preparation state or an exposure start state, the one or more target operations are operations of the flat-panel detector and are a window opening operation if the at least one exposure state is the exposure preparation state and are a signal acquisition operation if the at least one exposure state is the exposure start state;
    generating target operation instructions based on the one or more target operations of the first components; and
    controlling the first components to implement the target operation instructions.

2. The system of claim 1, the at least one processor is further directed to perform operations including:
    transmitting state information of the first components to a master control device after the first components preform the one or more target operations.

3. The system of claim 1, prior to the determining first components associated with the imaging device and one or more target operations of the first components corresponding to the at least one exposure state, the operations further including:
    determining a correspondence relationship between exposure states and operations of the first components; and
    determining the one or more target operations of the first components corresponding to the at least one exposure state based on the correspondence relationship.

4. The system of claim 1, wherein the at least one exposure state is obtained by dividing an exposure process of a radiation exposure on a subject into one or more phases, each of the one or more phases corresponding to an exposure state.

5. The system of claim 1, wherein the at least one exposure state further includes at least one of an exposure end state or an idle state.

6. The system of claim 1, wherein the at least one processor is further directed to perform operations including:
obtaining information of second components, wherein the second components include a high-voltage generator;
determining operations of the second components in the exposure process based on the information of the second components;
identifying one or more target operations of the second components corresponding to the at least one exposure state of the second components by separating the operations of the second components in the exposure process according to the at least one exposure state, wherein the at least one exposure state of the second components is the same as the at least one exposure state of the first components; and
generating target operation instructions for controlling the second components to implement the one or more target operations.

7. The system of claim 1, wherein the imaging device includes a digital breast tomosynthesis (DBT), a full-field digital mammography (FFDM), a computed tomography (CT) device, a digital radiography (DR), or a computed radiography (CR).

8. A system, comprising:
at least one storage storing a set of instructions; and
at least one processor configured to communicate with the at least one storage-, wherein when executing the set of instructions, the at least one processor is directed to perform operations including:
obtaining exposure triggering parameters;
determining an exposure state of an imaging device based on the exposure triggering parameters;
generating exposure instructions including the determined exposure state; and
transmitting the exposure instructions to first components for controlling the first components to perform one or more target operations corresponding to the determined exposure state of the exposure instructions, wherein the first components include a flat-panel detector, the determined exposure state includes at least one of an exposure preparation state or an exposure start state, the one or more target operations are operations of the flat-panel detector and are a window opening operation if the determined exposure state is the exposure preparation state and are a signal acquisition operation if the determined exposure state is the exposure start state.

9. The system of claim 8, wherein the exposure triggering parameters include first parameters for activating the exposure state and second parameters representing state information of the first components after the first components have performed a prior exposure instruction.

10. A method implemented on a computing device having at least one computer readable storage medium storing a set of instructions and at least one processor executing the set of instructions for controlling a radiation exposure on a subject, the method comprising:
obtaining exposure instructions including at least one exposure state of an imaging device;
determining first components associated with the imaging device and one or more target operations of the first components corresponding to the at least one exposure state of the exposure instructions, wherein the first components include a flat-panel detector, the at least one exposure state includes at least one of an exposure preparation state or an exposure start state, the one or more target operations are operations of the flat-panel detector and are a window opening operation if the at least one exposure state is the exposure preparation state and are a signal acquisition operation if the at least one exposure state is the exposure start state;
generating target operation instructions based on the one or more target operations of the first components; and
controlling the first components to implement the target operation instructions.

11. The method of claim 10, further including:
transmitting state information of the first components to a master control device after the first components preform the one or more target operations.

12. The method of claim 10, prior to the determining first components associated with the imaging device and one or more target operations of the first components corresponding to the at least one exposure state, further including:
determining a correspondence relationship between exposure states and operations of the first components; and
determining the one or more target operations of the first components corresponding to the at least one exposure state based on the correspondence relationship.

13. The method of claim 10, wherein the at least one exposure state is obtained by dividing an exposure process of a radiation exposure on a subject into one or more phases, each of the one or more phases corresponding to an exposure state.

14. The method of claim 10, wherein the at least one exposure state further includes at least one of an exposure end state or an idle state.

15. The method of claim 10, further including:
obtaining information of second components, wherein the second components include a high-voltage generator;
determining operations of the second components in the exposure process based on the information of the second components;
identifying one or more target operations of the second components corresponding to the at least one exposure state of the second components by separating the operations of the second components in the exposure process according to the at least one exposure state, wherein the at least one exposure state of the second components is the same as the at least one exposure state of the first components; and
generating target operation instructions for controlling the second components to implement the one or more target operations.

16. The method of claim 10, wherein the imaging device includes a digital breast tomosynthesis (DBT), a full-field digital mammography (FFDM), a computed tomography (CT) device, a digital radiography (DR), or a computed radiography (CR).

* * * * *